US007700076B2

(12) United States Patent
Tamarkin et al.

(10) Patent No.: US 7,700,076 B2
(45) Date of Patent: *Apr. 20, 2010

(54) PENETRATING PHARMACEUTICAL FOAM

(75) Inventors: Dov Tamarkin, Maccabim (IL); Doron Friedman, Karmei Yosef (IL); Meir Eini, Ness Ziona (IL)

(73) Assignee: Foamix, Ltd., Ness Ziona (IT)

( * ) Notice: Subject to any disclaimer, the term of this patent is extended or adjusted under 35 U.S.C. 154(b) by 1425 days.

This patent is subject to a terminal disclaimer.

(21) Appl. No.: 10/922,358

(22) Filed: Aug. 20, 2004

(65) Prior Publication Data
US 2005/0074414 A1    Apr. 7, 2005
US 2010/0040561 A9    Feb. 18, 2010

Related U.S. Application Data

(63) Continuation-in-part of application No. PCT/IB03/05527, filed on Oct. 24, 2003, application No. 10/922,358, which is a continuation-in-part of application No. 10/911,367, filed on Aug. 4, 2004.

(60) Provisional application No. 60/497,648, filed on Aug. 25, 2003, provisional application No. 60/429,546, filed on Nov. 29, 2002, provisional application No. 60/492,385, filed on Aug. 4, 2003.

(30) Foreign Application Priority Data
Oct. 25, 2002    (IL) .................................. 152486

(51) Int. Cl.
*A61K 9/12*    (2006.01)
*A61K 9/00*    (2006.01)
*A61K 8/02*    (2006.01)
*A61K 31/19*    (2006.01)
*A61K 31/17*    (2006.01)

(52) U.S. Cl. .................. 424/47; 424/43; 424/401; 514/945; 514/588; 514/557

(58) Field of Classification Search .................. 424/47, 424/43, 401; 514/945, 588, 557
See application file for complete search history.

(56) References Cited

U.S. PATENT DOCUMENTS

| | | |
|---|---|---|
| 3,092,255 A | 6/1963 | Hohman |
| 3,142,420 A | 7/1964 | Gawthrop |
| 3,149,543 A | 9/1964 | Naab |
| 3,301,444 A | 1/1967 | Wittke |
| 3,366,494 A | 1/1968 | Bower |
| 3,384,541 A | 5/1968 | Clark et al. |
| 3,401,849 A | 9/1968 | Weber, III |
| 3,419,658 A | 12/1968 | Naab |
| 3,574,821 A | 4/1971 | Pfirrmann et al. |
| 3,751,562 A | 8/1973 | Nichols |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,959,160 A | 5/1976 | Horsler et al. |
| 3,962,150 A | 6/1976 | Viola |
| 3,997,467 A | 12/1976 | Jederstrom et al. |
| 4,001,442 A | 1/1977 | Stahlberger et al. |
| 4,019,657 A | 4/1977 | Spitzer et al. |
| 4,145,411 A | 3/1979 | Mende |
| 4,241,149 A | 12/1980 | Labes et al. |
| 4,268,499 A * | 5/1981 | Keil ........................... 424/68 |
| 4,271,149 A | 6/1981 | Winicov et al. |
| 4,292,326 A | 9/1981 | Nazzaro-Porro et al. |
| 4,299,826 A | 11/1981 | Luedders |
| 4,323,694 A | 4/1982 | Scala, Jr. |
| 4,386,104 A | 5/1983 | Nazzaro-Porro |
| 4,447,486 A | 5/1984 | Hoppe et al. |
| 4,508,705 A | 4/1985 | Chaudhuri et al. |
| 4,529,601 A | 7/1985 | Broberg et al. |
| 4,627,973 A | 12/1986 | Moran et al. |
| 4,628,063 A | 12/1986 | Haines et al. |
| 4,672,078 A | 6/1987 | Sakai et al. |
| 4,741,855 A | 5/1988 | Grote et al. |
| 4,752,465 A | 6/1988 | Mackles |
| 4,808,388 A | 2/1989 | Beutler et al. |
| 4,822,613 A | 4/1989 | Rodero |

(Continued)

FOREIGN PATENT DOCUMENTS

| | | |
|---|---|---|
| DE | 933486 | 9/1955 |
| DE | 10138495 | 2/2003 |
| EP | 0 270 316 | 6/1988 |
| EP | 297436 | 1/1989 |
| EP | 0488089 A1 | 6/1992 |
| EP | 0 535 327 | 4/1993 |
| EP | 0598412 | 11/1993 |
| EP | 0738516 | 10/1996 |
| EP | 0824911 | 2/1998 |
| EP | 0979654 A1 | 2/2000 |

(Continued)

OTHER PUBLICATIONS

Martindale, The extra pharmacopoeia [28th] edition, Eds.: Reynolds, J.E.F. and Prasad, A.B., The Pharmaceutical Press, London, 1982, pp. 862-864.

(Continued)

*Primary Examiner*—Sreeni Padmanabhan
*Assistant Examiner*—Abigail Fisher
(74) *Attorney, Agent, or Firm*—Wilmer Cutler Pickering Hale and Dorr LLP

(57) ABSTRACT

The invention relates to an alcohol-free cosmetic or pharmaceutical foam composition comprising water, a hydrophobic solvent, a surface-active agent, a gelling agent, an active component selected from the group of urea, hydroxy acid and a therapeutic enhancer and a propellant. The foam further comprises active agents and excipients with therapeutic properties having enhanced skin penetration.

51 Claims, No Drawings

U.S. PATENT DOCUMENTS

| | | |
|---|---|---|
| 4,836,217 A | 6/1989 | Fischer et al. |
| 4,837,378 A | 6/1989 | Borgman |
| 4,847,068 A | 7/1989 | Dole et al. |
| 4,874,794 A | 10/1989 | Katz |
| 4,885,282 A | 12/1989 | Thornfeldt |
| 4,913,893 A | 4/1990 | Varco |
| 4,956,049 A | 9/1990 | Bernheim et al. |
| 4,970,067 A | 11/1990 | Panandiker et al. |
| 4,981,677 A | 1/1991 | Thau |
| 4,981,845 A | 1/1991 | Pereira |
| 4,992,478 A | 2/1991 | Geria |
| 5,002,680 A | 3/1991 | Schmidt et al. |
| 5,034,220 A | 7/1991 | Helioff et al. |
| 5,071,648 A | 12/1991 | Rosenblatt |
| 5,071,881 A | 12/1991 | Parfondry et al. |
| 5,087,618 A | 2/1992 | Bodor |
| 5,089,252 A | 2/1992 | Grollier et al. |
| 5,094,853 A | 3/1992 | Hagarty |
| 5,130,121 A | 7/1992 | Kopolow et al. |
| 5,133,972 A | 7/1992 | Ferrini et al. |
| 5,143,717 A | 9/1992 | Davis |
| 5,156,765 A | 10/1992 | Smrt |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,217,707 A | 6/1993 | Szabo et al. |
| 5,219,877 A | 6/1993 | Shah et al. |
| 5,254,334 A | 10/1993 | Ramirez et al. |
| 5,262,407 A | 11/1993 | Leveque et al. |
| 5,308,643 A | 5/1994 | Osipow et al. |
| 5,314,904 A | 5/1994 | Egidio |
| 5,326,557 A | 7/1994 | Glover et al. |
| 5,352,437 A | 10/1994 | Nakagawa |
| 5,385,943 A | 1/1995 | Nazzaro-Porro |
| 5,411,992 A | 5/1995 | Eini et al. |
| 5,435,996 A | 7/1995 | Glover et al. |
| 5,482,965 A | 1/1996 | Rajadhyaksha |
| 5,512,555 A | 4/1996 | Waldstreicher |
| 5,520,918 A | 5/1996 | Smith |
| 5,534,261 A | 7/1996 | Rodgers et al. |
| 5,536,743 A | 7/1996 | Borgman |
| 5,545,401 A | 8/1996 | Shanbrom |
| 5,589,515 A | 12/1996 | Suzuki et al. |
| 5,635,469 A | 6/1997 | Fowler et al. |
| 5,641,480 A | 6/1997 | Vermeer |
| 5,650,554 A | 7/1997 | Moloney |
| 5,672,634 A | 9/1997 | Tseng et al. |
| 5,679,324 A * | 10/1997 | Lisboa et al. ................. 424/45 |
| 5,700,396 A | 12/1997 | Suzuki et al. |
| 5,716,611 A | 2/1998 | Oshlack et al. |
| 5,719,197 A | 2/1998 | Kanios et al. |
| 5,730,964 A | 3/1998 | Waldstreicher |
| 5,733,558 A | 3/1998 | Breton et al. |
| 5,753,245 A | 5/1998 | Fowler et al. |
| 5,759,520 A | 6/1998 | Sachetto |
| 5,767,104 A | 6/1998 | Bar-Shalom et al. |
| 5,783,202 A | 7/1998 | Tomlinson et al. |
| 5,792,922 A | 8/1998 | Moloney et al. |
| 5,804,546 A | 9/1998 | Hall et al. |
| 5,817,322 A | 10/1998 | Xu |
| 5,833,960 A | 11/1998 | Gers-Barlag et al. |
| 5,837,270 A | 11/1998 | Burgess |
| 5,840,744 A | 11/1998 | Borgman |
| 5,843,411 A | 12/1998 | Hernandez et al. |
| 5,846,983 A | 12/1998 | Sandborn et al. |
| 5,877,216 A | 3/1999 | Place et al. |
| 5,889,028 A | 3/1999 | Sandborn et al. |
| 5,889,054 A | 3/1999 | Yu et al. |
| 5,911,981 A | 6/1999 | Dahms et al. |
| 5,914,310 A | 6/1999 | Li et al. |
| 5,922,331 A | 7/1999 | Mausner |
| 5,951,993 A | 9/1999 | Scholz et al. |
| 5,952,392 A | 9/1999 | Katy |
| 5,961,957 A | 10/1999 | McAnalley |
| 5,972,310 A | 10/1999 | Sachetto |
| 5,993,846 A | 11/1999 | Friedman et al. |
| 6,033,647 A | 3/2000 | Touzan et al. |
| 6,045,779 A | 4/2000 | Mueller et al. |
| 6,093,408 A | 7/2000 | Hasenoehrl et al. |
| 6,110,477 A | 8/2000 | Hernandez et al. |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,140,355 A | 10/2000 | Egidio et al. |
| 6,171,347 B1 | 1/2001 | Kunz |
| 6,180,669 B1 | 1/2001 | Tamarkin |
| 6,183,762 B1 | 2/2001 | Deckers et al. |
| 6,187,290 B1 | 2/2001 | Gilchrist et al. |
| 6,224,888 B1 | 5/2001 | Vatter et al. |
| 6,231,837 B1 | 5/2001 | Stroud et al. |
| 6,251,369 B1 | 6/2001 | Stoltz |
| 6,258,374 B1 | 7/2001 | Friess et al. |
| 6,294,550 B1 | 9/2001 | Place et al. |
| 6,299,900 B1 | 10/2001 | Reed et al. |
| 6,306,841 B1 | 10/2001 | Place et al. |
| 6,333,362 B1 | 12/2001 | Lorant |
| 6,358,541 B1 | 3/2002 | Goodman |
| 6,383,471 B1 | 5/2002 | Chen et al. |
| 6,410,036 B1 | 6/2002 | De Rosa et al. |
| 6,423,323 B2 | 7/2002 | Neubourg |
| 6,433,033 B1 | 8/2002 | Isobe et al. |
| 6,468,989 B1 | 10/2002 | Chang et al. |
| 6,514,487 B1 | 2/2003 | Barr |
| 6,524,594 B1 | 2/2003 | Santora et al. |
| 6,536,629 B2 | 3/2003 | van der Heijden |
| 6,544,530 B1 | 4/2003 | Friedman |
| 6,620,773 B1 | 9/2003 | Stork et al. |
| 6,730,288 B1 | 5/2004 | Abram |
| 6,765,001 B2 | 7/2004 | Gans et al. |
| 6,902,737 B2 * | 6/2005 | Quemin ..................... 424/401 |
| 6,946,120 B2 | 9/2005 | Wai-Chiu So et al. |
| 7,029,659 B2 | 4/2006 | Abram |
| 7,235,251 B2 | 6/2007 | Hamer et al. |
| 2002/0035046 A1 | 3/2002 | Lukenbach et al. |
| 2002/0058055 A1 | 5/2002 | Zecchino et al. |
| 2002/0072544 A1 | 6/2002 | Miller et al. |
| 2002/0098215 A1 | 7/2002 | Douin et al. |
| 2002/0117516 A1 | 8/2002 | Lasserre et al. |
| 2002/0182162 A1 | 12/2002 | Shahinpoor et al. |
| 2004/0063787 A1 | 4/2004 | Villanueva |
| 2004/0151671 A1 | 8/2004 | Abram et al. |
| 2004/0192754 A1 | 9/2004 | Shapira et al. |
| 2004/0241099 A1 | 12/2004 | Popp et al. |
| 2004/0265240 A1 | 12/2004 | Tamarkin et al. |
| 2005/0013853 A1 | 1/2005 | Gil-ad et al. |
| 2005/0042182 A1 | 2/2005 | Arkin et al. |
| 2005/0232869 A1 | 2/2005 | Tamarkin et al. |
| 2005/0079139 A1 | 4/2005 | Jacques et al. |
| 2005/0186142 A1 | 8/2005 | Tamarkin et al. |
| 2005/0186147 A1 | 8/2005 | Tamarkin et al. |
| 2005/0196414 A1 | 9/2005 | Dake et al. |
| 2005/0205086 A1 | 9/2005 | Tamarkin et al. |
| 2005/0222090 A1 | 10/2005 | Cheng et al. |
| 2005/0255048 A1 | 11/2005 | Hirsh et al. |
| 2005/0266035 A1 | 12/2005 | Healy et al. |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0285912 A1 | 12/2005 | Delametter et al. |
| 2006/0018937 A1 | 1/2006 | Tamarkin et al. |
| 2006/0018938 A1 | 1/2006 | Neubourg |

| | | | |
|---|---|---|---|
| 2006/0029565 A1 | 2/2006 | Xu et al. |
| 2006/0088561 A1 | 4/2006 | Eini et al. |
| 2006/0140984 A1 | 6/2006 | Tamarkin et al. |
| 2006/0193789 A1 | 8/2006 | Tamarkin et al. |
| 2006/0233721 A1 | 10/2006 | Tamarkin et al. |
| 2006/0269485 A1 | 11/2006 | Friedman et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2007/0020304 A1 | 1/2007 | Tamarkin et al. |
| 2007/0059253 A1 | 3/2007 | Popp et al. |
| 2007/0069046 A1 | 3/2007 | Eini et al. |
| 2007/0098647 A1 | 5/2007 | Neubourg |
| 2007/0253911 A1 | 11/2007 | Tamarkin et al. |
| 2007/0280891 A1 | 12/2007 | Tamarkin et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0069779 A1 | 3/2008 | Tamarkin et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2009/0041680 A1 | 2/2009 | Tamarkin et al. |
| 2009/0068118 A1 | 3/2009 | Eini et al. |
| 2009/0130029 A1 | 5/2009 | Tamarkin et al. |
| 2009/0175799 A1 | 7/2009 | Tamarkin et al. |
| 2009/0180970 A1 | 7/2009 | Tamarkin et al. |

FOREIGN PATENT DOCUMENTS

| | | |
|---|---|---|
| EP | 1055425 A2 | 11/2000 |
| EP | 1215258 | 6/2002 |
| EP | 1287813 | 3/2003 |
| EP | 1428521 | 6/2004 |
| EP | 1189579 | 9/2004 |
| EP | 1475381 | 11/2004 |
| EP | 1500385 | 1/2005 |
| EP | 1 584 324 | 11/2007 |
| EP | 1584324 | 11/2007 |
| FR | 2774595 A | 8/1999 |
| FR | 2915891 | 11/2008 |
| GB | 808104 | 1/1959 |
| GB | 808105 | 1/1959 |
| GB | 1026831 | 4/1966 |
| GB | 1397285 | 6/1975 |
| IL | 0152486 A0 | 5/2003 |
| JP | 2184614 | 7/1990 |
| JP | 5070340 | 3/1993 |
| JP | 5213734 | 8/1993 |
| JP | 6100414 | 4/1994 |
| JP | 6329532 | 11/1994 |
| JP | 2008040899 | 2/1996 |
| JP | 8165218 | 6/1996 |
| JP | 9110636 | 4/1997 |
| JP | 2000080017 | 3/2000 |
| JP | 2000128734 | 5/2000 |
| JP | 2002012513 | 1/2002 |
| WO | WO-86/05389 | 9/1986 |
| WO | WO-88/01863 | 3/1988 |
| WO | WO 91/11991 | 8/1991 |
| WO | WO-96/03115 | 2/1996 |
| WO | WO 96/19921 | 4/1996 |
| WO | WO 96/27376 | 9/1996 |
| WO | WO-96/39119 | 12/1996 |
| WO | WO-97/39745 | 10/1997 |
| WO | WO-98/18472 | 5/1998 |
| WO | WO-98/23291 | 6/1998 |
| WO | WO-99/08649 | 2/1999 |
| WO | WO-99/20250 | 4/1999 |
| WO | WO-98/19654 | 5/1999 |
| WO | WO-99/37282 | 7/1999 |
| WO | WO-00/09082 | 2/2000 |
| WO | WO 00/15193 | 3/2000 |
| WO | WO-00/61076 | 10/2000 |
| WO | WO-00/76461 | 12/2000 |
| WO | WO-01/08681 | 2/2001 |
| WO | WO 01/70242 A2 | 9/2001 |
| WO | WO-01/82880 | 11/2001 |
| WO | WO-02/00820 | 1/2002 |
| WO | WO-02/28435 | 4/2002 |
| WO | WO-02/41847 | 5/2002 |
| WO | WO-02/41847 A1 | 5/2002 |
| WO | WO 03/051294 | 6/2003 |
| WO | WO-03/053292 | 7/2003 |
| WO | WO-03/075851 | 9/2003 |
| WO | WO-2004/071479 A1 | 8/2004 |
| WO | WO 2004/112780 A1 | 12/2004 |
| WO | WO-2005/011567 A2 | 2/2005 |
| WO | WO-2005/018530 A2 | 3/2005 |
| WO | WO-2005/097068 A1 | 10/2005 |
| WO | WO-2006/003481 | 1/2006 |
| WO | WO-2006/010589 | 2/2006 |
| WO | WO-2006/091229 | 8/2006 |
| WO | WO-2006/100485 | 9/2006 |
| WO | WO-2006/129161 | 12/2006 |
| WO | WO-2007/085902 | 8/2007 |
| WO | WO-2008/008397 | 1/2008 |
| WO | WO-2008/038147 | 4/2008 |
| WO | WO-2008/075207 | 6/2008 |
| WO | WO-2008/087148 | 7/2008 |

OTHER PUBLICATIONS

Wormser et al. *Letters to the* Editor, Burns, 1998, 24, 383.

Wormser et al. Arch. Toxicol., 1997, 71, 165-170.

U.S. Appl. No. 10/835,359, Tamarkin et al., Foamable Iodine Compositions, filed Apr. 28, 2004.

U.S. Appl. No. 10/911,367, Tamarkin et al., Foam Carrier Containing Amphiphilic Copolymer Gelling Agent, filed Aug. 4, 2004.

U.S. Appl. No. 10/922,555, Tamarkin et al., Foam Incorporating Eutectic Mixture, filed Aug. 20, 2004.

U.S. Appl. No. 10/835,505, Tamarkin et al., Oleaginous Pharmaceutical and Cosmetic Foam, filed Apr. 28, 2004.

Barry, B.W. et al, Comparative bio-availability and activity of proprietary topical corticosteroid preparations: vasoconstrictor assays on thirty-one ointments, British Journal of Dermatology, 93, 563-571, 1975.

Tamarkin, D., et al. Body Cavity Foam, U.S. Appl. No. 11/116,761, filed Apr. 28, 2005.

Tamarkin, D., et al. Moisturizing Foam Containing Lanolin, U.S. Appl. No. 11/099,942, filed Apr. 6, 2005.

Tamarkin, D., et al. Nonsteroidal Immunomodulating Kit and Composition and Uses Thereof, U.S. Appl. No. 11/078,902, filed Mar. 11, 2005.

Tamarkin, D., et al. Steroid Kit and Foamable Composition and Uses, U.S. Appl. No. 11/114,410, filed Apr. 26, 2005.

Tamarkin, D., et al. Vasoactive Kit and Composition and Uses Thereof, U.S. Appl. No. 11/124,676, filed May 9, 2005.

Benet, et al., App-lication of NMR for the Determination of HLB Values of Nonionic Surfactants, Journal of the American Oil Chemists Society, vol. 49, 1972, 499-500.

Carbowax 1000MSDS; http://www.sciencelab.com/xMSDS-Polyethylene_glycol_1000-9926622. Accessed Dec. 13, 2008, 6 pages.

Cheshire, et al., Disorders of Sweating, www.medscape.com, Semin Neurol 23(4):399-406, 2003.

Dalby, "Determination of Drug Solubility in Aerosol Propellants," Pharmaceutical Research, vol. 8, No. 9, 1991, pp. 1206-1209.

Emulsifiers with HLB values. http://www.theherbarie.com/files/resources-centers/formulating/Emulsifiers_HLB_Values.pdf accessed Aug. 5, 2009 (3 pps).

Glaser, et al., Hyperhidrosis: A Comprehensive and Practical Approach to Patient Management, Expert Rev. Dermatol. 1(6), 773-775 (2006).

Hashim, et al. "Tinea versicolor and visceral leishmaniasis," Int J Dermatol., Apr. 1994; 33(4), pp. 258-259 (abstract only).

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd (30 Pages), 1999.

hydroxyethylcelllulose. htt;://terpconnect.umd.edu/~choi/MSDS/Sigma-Aldrich/HYDROXYETHYL%20CELLULOSE, 5 pages, Jan. 14, 2004.

Kalkan, et al., The Measurement of Sweat Intensity Using a New Technique, Tr. J. of Medical Sciences 28, 515-517 (1998).

Kathon™ CG (product information sheet by Rohm and Haas, Jun. 2006).

Kinnunen, Contact Dermatitis Sep. 1989; 21(3): 154-8.

Metronidazole. www.usp.org/pdf/EN/veterinary/metronidazole.pdf. accessed Sep. 10, 2009, 4 pages.

OM Cinnamate. http://www.makingcosmetics.com/sunscreens/OM-Cinnamate-p102.html accessed Sep. 26, 2009.

Progesterone MSDS. http://www.usp.org.pdf.EN/referenceStandards/msds/1568007.pdf on Dec. 14, 2002, 5 pages.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-24 (abstract).

Shear, et al., "Pharmacoeconomic analysis of topical treatments for tinea infections," Pharmacoeconomics. Mar.1995; 7(3); pp. 251-267 (abstract only).

Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Torres-Rodriguez, JM., "New topical antifungal drugs," Arch Med Res. 1993 Winter; 24(4), pp. 371-375 (abstract).

* cited by examiner

PENETRATING PHARMACEUTICAL FOAM

RELATED APPLICATIONS

The invention claims priority under 35 U.S.C. § 119(e) to U.S. Ser. No. 60/497,648, filed Aug. 25, 2003, which is hereby incorporated in its entirety by reference.

This application is a continuation-in-part of International Patent Application No. IB03/005527 designating the United States and filed on Oct. 24, 2003, which claims the benefit of priority under 35 U.S.C. §119(e) to U.S. patent application Ser. No. 60/429,546, filed on Nov. 29, 2002, entitled "Cosmetic and Pharmaceutical Foam."

This application is a continuation-in-part application of co-pending U.S. patent application Ser. No. 10/911,367, filed on Aug. 4, 2004, which claims the benefit of priority under 35 U.S.C. §119(e) to U.S. patent application Ser. No. 60/492,385, filed on Aug. 4, 2003, both entitled "Foam Carrier Containing Amphiphilic Copolymer Gelling Agent."

FIELD OF THE INVENTION

The invention relates to an alcohol-free cosmetic or pharmaceutical foam carrier comprising water, a hydrophobic solvent, a surface-active agent and a gelling agent. The foam carrier further comprises active agents and excipients providing beneficial therapeutic properties.

BACKGROUND OF THE INVENTION

Foam products are used for topical applications of drugs and cosmetics. Aerosol products and particularly foams are complicated physical-chemical structures that do not form under arbitrary circumstances. In particular, a special balance between the foam-forming components is important. Slight shifts in the composition may already result in a collapse of the foam; thus, a formulation of per se active substances may not be capable of being formulated as a foam without further provisions.

The inventors of the present invention have developed a series of novel emulsion-based foam formulations. See, for example, commonly assigned, co-pending application WO 2004/037225.

U.S. Pat. No. 6,423,323 describes a foam skin cream, which optionally contains urea and lactic acid. The skin cream formulation is limited to a very specific list of ingredients that are not contemplated in the present invention.

U.S. Pat. No. 4,145,411 describes shaving foam compositions with low levels of mineral oil (0.25-1% by weight) and urea (0.001-0.006% by weight). A shaving foam is, by definition, not breakable and thus cannot readily facilitate topical administration of an active ingredient and especially is not well-suited for topical administration of compositions geared towards skin penetration.

SUMMARY OF THE INVENTION

In one aspect of the present invention, an alcohol-free cosmetic or pharmaceutical foamable composition containing at least one active component, selected from the group of: (1) urea, in a concentration of at least 2%; (2) a hydroxy acid in a concentration of at least 1%; and (3) a therapeutic enhancer is provided, which upon admixing with a liquefied gas propellant in an aerosol container releases a breakable foam that is suitable for topical administration. The alcohol-free foam composition is suitable for inclusion of both water-soluble and oil-soluble active agents. As used herein, a foamable composition includes formulations that are capable of forming a foam when dispensed from an aerosol container.

The cosmetic or pharmaceutical foamable composition according to one or more embodiments of the present invention includes water, a hydrophobic solvent, a surface-active agent and a gelling agent and at least one active component selected from the group of (1) urea in a concentration of at least 2%; (2) a hydroxy acid in a concentration of at least 1%; and (3) a therapeutic enhancer in a concentration of at least 2%; and a liquefied gas propellant in the amount of about 3-18% by weight of the total composition.

Such a composition creates an oil-in-water emulsion that is stable in its pre-dispensed state. Upon release from the aerosol container, the composition forms a breakable foam product, which is suitable for topical or mucosal administration.

In one or more embodiments of the present invention, the hydrophobic solvent is included in the foamable composition at a concentration of 5% to about 10% (Class A), or 10% to about 20% (Class B), or about 20% to about 50% (Class C). The surface-active agent concentration is about 0.1% to about 5%; the concentration of the gelling agent is 0.01% to about 5% by weight and the liquefied gas propellant is included at a concentration of about 3% to about 18% of the total composition. Water and optional ingredients are added to complete the total mass to 100%. Yet, in other embodiments, as specified herein, foamable composition, the hydrophobic solvent content can be between 0% and 5%.

In one or more embodiments, each of the above compositions further optionally comprises a foam adjuvant in the concentration range of 0.1% to 5%.

The foamable composition does not contain short chain aliphatic alcohols, making it non-irritant and non-drying.

In one or more embodiments, a foamable composition is provided that includes a foamable composition as described herein and further includes at least one active agent at a therapeutically effective concentration. The foam carrier is suitable for inclusion of both water-soluble and oil-soluble active agents, as well as suspended active agents. Such a composition is suitable for topical treatment of human and animal skin and mucosal disorders or diseases. Alternatively, the composition is suitable for cosmetic treatment, for example, for cleansing, beautifying, promoting attractiveness or altering the appearance without affecting the body structure or function.

In addition, cosmetic and medical disorders are identified that are best treated using the alcohol-free foam carrier and the alcohol-free cosmetic or pharmaceutical composition, and the advantages of such carrier and products are demonstrated.

The foam carrier or composition according to one or more embodiments of the present invention provides various advantages over current foam compositions.

1. The foam is lightweight and thus, economical.
2. The foam contains a hydrophobic solvent, in desirable concentration, which provides a refatting and skin soothing effect.
3. The foam can include water-soluble, oil-soluble active and suspended agents.
4. The foam is easily spreadable, allowing treatment of large areas such as the arms, back, legs and the breast.
5. Due to flow properties of the foam, the foam spreads effectively into folds and wrinkles, thereby providing uniform distribution and absorption of the active agent without the need of extensive rubbing.

As used herein, all component percentages are reported as percent by weight of the total composition.

As used herein, the term "about" when used to refer to weight % in a composition means ±10% of the reported weight %. As used herein, the term "about" when used to refer to measured characteristics of the composition means ±20% of the reported value.

DETAILED DESCRIPTION OF THE INVENTION

Hydrophobic Solvent

The foamable composition includes a hydrophobic solvent. The hydrophobic solvent includes a material having solubility in distilled water at ambient temperature of less than about 1 gm per 100 mL, or less than about 0.5 gm per 100 mL, or less than about 0.1 gm per 100 mL. The hydrophobic solvent is a liquid at ambient (room) temperature, e.g., about 20-30° C.

The total content of hydrophobic solvent may vary from 5% to 50% (w/w). However, different ranges (herein "composition Classes A-C") have been designated, in order to facilitate a choice of an appropriate class, according to the anticipated cosmetic or pharmaceutical need. As a rule of thumb, higher hydrophobic solvent concentrations are more appropriate for the treatment of dry skin, and/or for the treatment of a disease, which is more responsive to drugs, delivered in an oily vehicle and regulating the residence of an active ingredient in the target area. Another consideration relates to the usability and tolerability of the product, whereby very high concentration of the hydrophobic solvent (from about 25% of the composition) would leave an oily feeling subsequent to application, which is undesirable in the product. Thus, when using a foamable composition, the hydrophobic solvent concentration is selected in view of the target treated population and the specific needs of the intended treated population.

In one embodiment, the hydrophobic solvent is mineral oil. Mineral oil (Chemical Abstracts Service Registry number 8012-95-1) is a mixture of aliphatic, naphthalenic, and aromatic liquid hydrocarbons that derive from petroleum. They are typically liquid, their viscosity is in the range of between about 35 CST and about 100 CST (at 40° C.), and their pour point (the lowest temperature at which an oil can be handled without excessive amounts of wax crystals forming so preventing flow) is below 0° C. By contrast, white petrolatum, also termed "Vaseline", is disadvantageous, due to the waxy nature of petrolatum. It is known to leave waxy and sticky feeling after application and occasionally stain cloths. Thus, white petrolatum is not a preferred hydrophobic solvent according to the present invention.

Yet other hydrophobic solvents include, but are not limited to, liquid oils from vegetable, marine or animal sources. Preferably, the unsaturated oil is selected from the group consisting of an olive oil, a corn oil, a soybean oil, a canola oil, a cottonseed oil, a coconut oil, a sesame oil, a sunflower oil, a borage seed oil, an syzigium aromaticum oil, a hempseed oil, a herring oil, a cod-liver oil, a salmon oil, a flaxseed oil, a wheat germ oil, an evening primrose oil and any mixtures thereof, at any proportion.

A particular class of oils includes polyunsaturated oils, containing omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Thus, in a particular embodiment of the present invention the unsaturated oil contains at least 6% of an oil selected from omega-3 oil, omega-6 oil, and mixtures thereof.

Another class of oils is essential oils, which are considered "therapeutic oils" containing active biologically occurring molecules, which, upon topical application, exert a therapeutic effect. Examples of such oils are rosehip oil, which contain retinoids and is known to reduce acne and post-acne scars, tea tree oil, which possesses antibacterial, antifungal and antiviral properties. Other examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil, know in the art of herbal medication.

Another class of solvents includes, but is not limited to, liquid hydrophobic plant-derived oils, which are known to possess therapeutic benefits when applied topically.

A further class of hydrophobic solvents is known as the group of "emollients". Without derogating the generality of this definition, examples of suitable emollients for use include isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, triisocetyl citrate, octyl dodecanol, sucrose esters of fatty acids, octyl hydroxystearate and mixtures thereof. Other examples of other suitable emollients can also be found in the Cosmetic Bench Reference, pp. 1.19-1.22 (1996).

In a particular embodiment, the hydrophobic solvent comprises a mixture of mineral oil and an emollient in a ratio between 2:8 and 8:2 on a weight basis.

Silicone oils are known for their skin protective properties and may be used as a hydrophobic solvent. The silicone oil is either a volatile silicon oil or a non-volatile silicone oil, wherein water-soluble silicones, such as dimethicone copolyol are not included in the definition of silicone oils (as hydrophobic solvents).

In a particular embodiment, the hydrophobic solvent includes at least 2% silicone oil.

One or more hydrophobic solvents in any combination can be used.

Surface-Active Agents

The foamable composition includes a surface-active agent. Surface-active agents (surfactants) include any agent that alters the surface properties of the oil and water components in the composition to aid in the formation of an emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers tend to form water-in-oil (w/o) emulsions; hydrophilic surfactants tend to form oil-in-water (o/w) emulsions. The HLB of a blend of two emulsifiers equals the weight fraction of emulsifier A times its HLB value plus the weight fraction of emulsifier B times its HLB value (weighted average).

Any surface-active agent, selected from anionic, cationic, non-ionic, zwitterionic, amphoteric and ampholytic surfactants, or combinations thereof may be used as surface-active agent. According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition is a single surface active agent having an HLB value between about 9 and 14, and in one or more embodiments, the foam composition contains more than one surface active agent and the weighted average of their HLB values is between about 9 and about 14.

Non-limiting examples of surfactants include polysorbates, such as polyoxyethylene (20) sorbitan monostearate (Tween 60) and polyoxyethylene (20) sorbitan monooleate (Tween 80); Polyoxyethylene (POE) fatty acid esters, such as Myrj 45, Myrj 49 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and sorbitol anhydrides, such as sorbitan monolaurate and sorbitan monolaurate-mono or diglycerides, isoceteth-20, sodium methyl cocoyl taurate, sodium methyl oleoyl taurate, sodium lauryl sulfate, triethanolamine lauryl sulfate and betaines.

In some embodiments, the surface-active agent is a non-ionic surfactant. Exemplary non-ionic surfactants include mono-, di- and tri-esters of sucrose with food fatty acids (sucrose esters), prepared from sucrose and methyl and ethyl esters of food fatty acids or by extraction from sucroglycerides. Further examples are sucrose esters with high monoester content, which have higher HLB values.

A combination of a non-ionic surfactant and an ionic surfactant (such as sodium lauryl sulphate) may be used. In one example, a non-ionic surfactant and an ionic surfactant are present in the foam carrier or composition at a ratio of between 1:1 and 20:1 or between 4:1 and 10:1.

Unlike prior art foamable compositions, low total amounts of surfactant are employed to obtain a stable foam. Surprisingly, lower surfactant levels are required to obtain a stable foamable composition, which is preferred in order to reduce skin irritations. Total surfactant level is in the range of about 0.1% to 5% by weight of the foamable composition, and can be less than 2% by weight or even less than 1% by weight. Thus, according to one or more embodiments, the ratio between the surface active agent and the hydrophobic solvent is between about 1:8 and about 1:16 or between about 1:16 and about 1:32.

Foam Adjuvants

Foam adjuvants may optionally be included in the foam composition and include fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). The concentration of the fatty alcohol, required to support the foam system is inversely related to the length of its carbon chains. Fatty alcohols derived from beeswax including a mixture of alcohols, a majority of which has at least 20 carbon atoms in their carbon chain, are especially well suited as foam adjuvants.

Another class of foam adjuvants includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof.

Optionally, the carbon atom chain of the fatty alcohol or the fatty acid may have at least one double bond. A further class of foam adjuvant includes a long chain fatty alcohol or fatty acid, wherein the carbon atom chain is branched. In a further class of foam adjuvants, the carbon chain of the fatty acid is substituted with a hydroxyl group, such as 12-hydroxy stearic acid.

The foam adjuvant may include a mixture of fatty alcohols, fatty acids and hydroxy fatty acids and derivatives thereof in any proportion, providing that the total amount is 0.1% to 5% (w/w) of the carrier mass. The total amount can be 0.4%-2.5% (w/w) of the carrier mass.

Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the pharmaceutical or cosmetic composition containing therapeutic foam adjuvant provides an extra therapeutic benefit in comparison with currently used vehicles, which are inert and non-active.

Gelling Agents

Gelling agents include, but are not limited to, naturally-occurring polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), micro-crystalline cellulose and compositions (Avicel types) manufactured by FMC, polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Optionally, mixtures of the above compounds are contemplated.

Also useful herein are gelling agents such as the acrylic acid/ethyl acrylate copolymers and the carboxyvinyl polymers sold, for example, by the B.F. Goodrich Company under the trademark of Carbopol Registered TM resins. These resins consist essentially of a colloidally water-soluble polyalkenyl polyether crosslinked polymer of acrylic acid crosslinked with from 0.75% to 2% of a crosslinking agent such as polyallyl sucrose or polyallyl pentaerythritol. Examples include Pemulene TR1 and TR2, Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule.

In one aspect of the invention, the gelling agent is selected from the class of amphiphilic copolymers. Amphiphilic copolymers include polymers having hydrophobic groups and hydrophilic groups or regions. These materials are referred to alternatively as "polymeric surfactants" because the hydrophilic and hydrophobic regions of the polymers serve to interact with and stabilize hydrophilic and lipophilic components, respectively, of a composition. The copolymer may be a random copolymer, a block copolymer of a graft or comb copolymer. Exemplary amphiphilic copolymers include di-, tri- or multi-block copolymer or graft copolymer of a biodegradable polymer.

The Amphiphilic copolymer may be an acrylate copolymer, in which hydrophobic moieties are chemically linked to hydrophilic polymer or hydrophilic moieties are attached to hydrophobic polymers to produce amphiphilic surface active and surface stabilizing agent. By way of example, suitable amphiphilic copolymers include cross linked copolymers of acrylic acid and a hydrophobic comonomer, such as Pemulen TR-1 and Pemulen TR-2, ETD 2020 and Carbopol 1382 (all, Acrylates/C10-30 alkyl acrylate crosspolymer), Natrosol CS Plus 330 and 430 and Polysurf 67 (all, cetyl hydroxyethyl cellulose), Aculyn 22 (acrylates/steareth-20 methacrylate copolymer), Aculyn 25 (acrylates/laureth-25 methacrylate copolymer), Aculyn 28 (acrylates/beheneth-25 methacrylate copolymer), Aculyn 46 (PEG-150/stearyl alcohol/SMDI copolymer), Stabylen 30 (acrylates/vinyl isodecanoate), Structure 2001 (acrylates/steareth-20 itaconate copolymer), Structure 3001 (acrylates/ceteth-20 itaconate copolymer) and Structure Plus (acrylates/aminoacrylates/C10-30 alkyl PEG 20 itaconate copolymer), where PEG is polyethylene glycol, PPG is polypropylene glycol.

Other exemplary amphiphilic copolymers include silicone polymers such as amphiphilic silicone polyols or copolyol, for example cetyl dimethicone copolyol and dimethicone copolyol PPG-3 oleyl ether, acetylated starch derivatives, amphiphilic modified starches, and amphiphilic block copolymers of ethylene oxide, propylene oxide and/or propylene glycol (also known as "poloxamer").

One or more gelling agents in any combination can be used.

The gelling agent is present in the foam composition in an amount of about 0.1% to 5.0%. In one or more embodiments, the gelling agent included in the foamable composition can be less than 1% of the foamable composition.

Active Component

According to one or more embodiments, urea is included in the foam composition as an active component.

Urea has been long recognized as a cosmetic ingredient in formulations acting as a humectant and moisturizer. There have been reports of keratolytic activity attributed to urea with the ability at high concentrations to solubilize and denature protein. High concentrations of urea are also known to have a mild, antimicrobial effect. Urea further possesses skin exfoliating properties, which are useful in the control of passage of active agents through the dermal barrier.

Urea preparations, especially those containing high urea concentration are provided in gels, creams, lotions and pastes, but not in foam. Foam is preferable in many cases where urea is needed for therapy. For example, xerosis, which is a common indication for high concentration urea preparations, is disseminated over large skin areas, and thus, the foam of the present invention, having low specific gravity and excellent spreading and absorption properties is advantageous.

In one embodiment, urea is contained in the foam composition in an amount from about 1% to about 50% of the total composition. Preferably compositions contain from about 10% to about 20%, and from about 20% to about 50%, depending on the intended use.

Because of its keratolytic effect, urea can serve as means to induce dermal penetration of a variety of drugs or cosmetic active agents. Furthermore, in many dermatological disorders, having urea, with its beneficial properties as mentioned above and a drug or cosmetic active agent provides a synergistic therapeutic effect. This is also the case when urea, which is known for its antibacterial and antifungal effects, is combined with another anti-infective agent.

Thus, in one or more embodiments of the present invention, the foamable composition includes urea and at least one pharmaceutical or cosmetic active agent, as defined hereinbelow. The penetration of the active agent is enhanced due to the urea present in the foam composition.

Hence, a foam according to the present invention includes a foamable composition containing urea in a therapeutically—effective concentration. In one embodiment, the foamable composition forms an emulsion of oil and water including a hydrophobic solvent at a level described herein as Class A, Class B, or Class C.

According to one or more embodiments, a hydroxy acid is included in the foam composition as an active component.

Hydroxy acids are useful in increasing the clarity of the skin surface, increasing cellular turnover, and increasing skin radiance and smoothness. They further possess skin exfoliating properties, which are useful in the control of passage of active agents through the dermal barrier.

Suitable hydroxy acids include alpha- or beta-hydroxy acids, poly-hydroxy acids, or any combinations of any of the foregoing. The hydroxy acid can be an alpha-hydroxy acid. Non-limiting examples of alpha hydroxy acids include, but are not limited to, glycolic acid, lactic acid, malic acid, citric acid, alpha-hydroxyethanoic acid, alpha-hydroxyoctanoic acid, alpha-hydroxycaprylic acid, hydroxycaprylic acidglycolic acid, tartaric acid, pyuric acid, citric acid, as well as their corresponding salts and pharmaceutically-acceptable derivatives; or any combination of any of the foregoing.

Ascorbic acid has skin permeation and collagen synthesis activity. Beta-hydroxy acids include, but are not limited to, salicylic acid, beta hydroxybutanoic acid, tropic acid and trethocanic acid.

Because of its keratolytic effect, hydroxy acids can serve as means to induce dermal penetration of a variety of drugs or cosmetic active agents. Furthermore, in many dermatological disorders, having urea, with its beneficial properties as mentioned above and a drug or cosmetic active agent provides a synergistic therapeutic effect.

Thus, in one or more embodiments of the present invention, the foamable composition comprises a hydroxy acid and at least one pharmaceutical or cosmetic active agent, as defined hereinbelow.

In one embodiment, the hydroxy acid is contained in the foamable composition in an amount from about 1% to about 30% of the total composition. The compositions can contain from about 1% to about 10% and from about 10% to about 30%, depending on their designated use.

According to one or more embodiments, a therapeutic enhancer is included in the foam composition as an active component. In the context of the present invention, a therapeutic enhancer is a material that facilitates an enhanced delivery of an active agent into a target site of treatment, thus enabling an improved therapeutic effect. Suitable therapeutic enhancers include polyhydric alcohols having at least two hydroxy groups, or at least three hydroxy groups, or a derivative of a polyhydric alcohol.

Non-limiting examples are propylene glycol, butylene glycols, glycerol, pentaerythritol, sorbitol, mannitol, oligosaccharides, dimethyl isosorbide, monooleate of ethoxylated glycerides (with 8 to 10 ethylene oxide units), polyethylene glycol 200-600, transcutol (diethylene glycol monoethyl ether) and glycofurol (tetrahydrofurfuryl alcohol PEG ether). The therapeutic enhancer can further comprise at least cyclodextrins a related compounds. Cyclodextrins are structurally related cyclic oligomaltoses, which form a new group of pharmaceutical excipients. These are torus-shaped molecules with a hydrophilic outer surface and a lipophilic central cavity. Cyclodextrins are capable of forming water-soluble inclusion complexes with a wide variety of lipophilic water-insoluble drugs by taking up a whole drug molecule, or some part of it, into the cavity. The cyclodextrin molecules are relatively large (molecular weight ranging from almost 1000 to over 1500), with a hydrated outer surface, and under normal conditions, cyclodextrin molecules will only permeate the skin barrier with considerable difficulty. It is generally believed that the cyclodextrin molecules act as true carriers by keeping lipophilic drug molecules in solution and deliver them to the skin surface where they partition from the cyclodextrin cavity into the skin.

In one embodiment, the therapeutic enhancer is contained in the foamable composition in an amount from about 2% to about 30% of the total composition. The compositions can contain from about 2% to about 10% and from about 10% to about 30%, depending on their designated use.

Active Agents

The foam composition is useful and advantageous for the treatment of skin disorders and for skin care and cosmetic care. The addition of an oil having refatting, protective and moisture-retaining properties in a spreadable foam form can substitute for currently available dermatological and cosmetic creams, lotions, gels, etc.

In one or more embodiments of the present invention, the foam composition includes an active agent directed to the treatment of a medical disorder or a cosmetic disorder. The active agent can be categorized by the benefit it provides or by its postulated mode of action. The active agents can in some instances provide more than one benefit or operate via more than one mode of action. Therefore, classifications are made for the sake of convenience and are not intended to limit the active to that particular application or applications listed. Furthermore, foam compositions, with or without further active ingredients, are suitable for the application as "cosmeceutical" preparations.

Antibacterial Agents

One class of drugs comprises antibacterial agents. The term "antibacterial" as used herein shall include, but is not limited to, any substance being destructive to or inhibiting the growth of bacteria or any substance having the capacity to inhibit the growth of or to destroy bacteria and other microorganisms, and are used in the treatment of infectious diseases. It is well known that bacterial infections are involved in a variety of superficial disorders of the skin, eye, mucosal membrane, oral cavity, vagina and rectum. The antibacterial drug can be active against gram positive and gram-negative bacteria, protozoa, aerobic bacteria and unaerobic ones.

The antibacterial drug is selected from the group consisting of chloramphenicol, tetracyclines, synthetic and semi-synthetic penicillins, beta-lactams, quinolones, fluoroquinolines, macrolide antibiotics, metronidazole and metronidazole derivatives and analogs, dicarboxylic acids, such as azelaic acid, silicylates, peptide antibiotics, cyclosporines and any combination thereof at a therapeutically effective concentration. Another group of antibacterial agents is non-specific and includes strong oxidants and free radical liberating compounds, such as hydrogen peroxide, bleaching agents (e.g., sodium, calcium or magnesium hypochlorite and the like) iodine, chlorohexidine and benzoyl peroxide.

Exemplary foamable compositions are particularly useful and beneficial in the prevention and treatment of secondary infections, accompanying skin-structure damage, such as in cuts, wounds, burns and ulcers. In all such cases, the present formulation is easy to use, being in foam state when applied and becoming liquid upon rubbing onto the skin.

While being useful in the prevention and treatment of infections, the antibacterial foam is also applicable for decontaminating areas, afflicted with bacterial warfare organisms, such as anthrax and smallpox.

Anti-Fungal Agents

Fungal infections are another object of treatment using the foamable composition. Superficial fungal infection of the skin is one of the commonest skin diseases seen in general practice. Dermatophytosis is probably the most common superficial fungal infection of the skin. Dermatophytosis is caused by a group of fungi capable of metabolizing the keratin of human epidermis, nails or hair. There are three genera of dermatophytes causing dermatophytosis, i.e., microsporum, *trichophyton* and *epidermophyton*.

Candidiasis is an infection caused by the yeast like fungus *candida albicans* or occasionally other species of candida. Clinical syndromes of candidiasis include: (a) oral candidiasis (oral thrush); (b) candidiasis of the skin and genital mucous membrane; (c) candida paronychia, which inflicts the nail; and (d) genital and vaginal candida, which inflict genitalia and the vagina.

The pharmaceutical composition can include an antifungal drug that is effective against dermatophytes and candida. The antifungal drug is selected from the group consisting of azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration.

The foam composition according to one or more embodiments of the present invention is useful, for example, for the treatment of tinea corporis, tinea pedis, tinea rubrum, tinea unguium, tinea cruris, tinea barbae and tinea versicolor, as well as yeast Infections, such as candidiasis, and candidal vaginitis.

Anti-Viral Agents

Any known antiviral drugs, in a therapeutically effective concentration, can be incorporated into the foam composition. Exemplary compositions are particularly beneficial in the case of viral infections. Cold sores are caused by the herpes simplex Type 1 virus and are sometimes referred to as facial herpes. Mollusca are small viral growths that appear singly or in groups on the face, trunk, lower abdomen, pelvis, inner thighs, or penis. Shingles (herpes zoster) usually occurs only once in a lifetime, appears as a rash (clusters of blisters with a red base). Shingles is caused by the same virus that is responsible for chickenpox. Warts are a common, benign skin tumor caused by viral infection.

Anti-Inflammatory and Antiallergic Agents

The active agent can be an anti-inflammatory or antiallergic agent. Exemplary anti-inflammatory or antiallergic agents include corticosteroids, non-steroidal anti-inflammatory drugs (NSAIDs), anti-histamines, immunosuppressants and any combination thereof at a therapeutically effective concentration.

The anti-inflammatory active agent is a corticosteroid. The corticosteroid can be selected from the group consisting of clobetasol proprionate, halobetasol proprionate, betamethasone diproprionate, betamethasone valerate, fluocinolone acetonide, halcinonide, betamethasone valerate, fluocinolone acetonide, hydrocortisone valerate, triamcinolone acetonide, hydrocortisone and any combination thereof at a therapeutically effective concentration. Since corticosteroid drugs are typically hydrophobic, suitable foam carriers include high levels of a hydrophobic solvent. The hydrophobic solvent facilitates topical distribution and enhances the rate of penetration of any of the corticosteroid drugs.

The composition may include active agents for the treatment of psoriasis. Corticosteroid ointments, greasy preparations containing little or no water, are commonly used for treating psoriasis. Their main disadvantage is in a sticky feeling subsisting for extended periods subsequent to treatment being completed thereby creating a latent inconvenience and possible discomfort to the treatment recipient. In contrast, the foam composition according to one or more embodiments of the present invention containing high levels of an oil (hydrophobic solvent) spreads very easily throughout the afflicted area and absorbs into the skin without leaving any unpleasant sensation or look. Examples of other inflammatory disorders that are treatable by a foamable composition including a steroid as an active agent are atopic dermatitis, seborrhea, seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pityriasis rosea and pemphigus.

Topical antihistaminic preparations currently available include 1% and 2% diphenhydramine (Benadryl® and Caladryl®), 5% doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines, can also be used.

Polyunsaturated fatty acids containing omega-3 and omega-6 fatty acids (e.g., linoleic and linolenic acid, gamma-linoleic acid (GLA), eicosapentaenoic acid (EPA) and docosahexaenoic acid (DHA) also are beneficial in the treatment of psoriasis and other skin inflammation conditions and may be included in the foamable composition.

Nonsteroidal anti-inflammatory agents (NSAIDs) are useful against skin and systemic bio-abnormalities and can be added to the foam composition. The variety of compounds encompassed by NSAIDs is well-known to those skilled in the art. Specific non-steroidal anti-inflammatory agents useful in the composition include, but are not limited to oxicams, such as piroxicam, isoxicam, tenoxicam, sudoxicam; salicylates, such as salicylic acid, ethyl salicylate, methyl salycilate, aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Any other steroidal and nonsteroidal compounds having the capacity to prevent, alleviate the symptoms of, treat or cure inflammation processes, may be generally included as anti-inflammatory agents.

The pharmaceutical composition may include an anti-inflammatory and/or an antiallergic agent that reduces the occurrence of pro-inflammatory cytokines or inhibits the effect of pro-inflammatory cytokines.

Mixtures of any anti-inflammatory agents can be used in the composition, as well as the dermatologically acceptable salts, esters, amides, prodrugs and derivatives of these agents.

Topical application of a foam, comprising a safe and effective dose of an NSAID can be useful in the prevention and/or alleviation of the symptoms of rheumatoid arthritis, osteoarthritis and pain. Topical NSAIDs, incorporated in the foam composition can be also used in the treatment of dermatological disorders such as acne, rosacea, hair growth disorders, actinic keratosis and certain skin cancer conditions.

Local Anesthetics

The foam compositions may include an effective amount of a topical anesthetic. The topical anesthetic can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated Keratolytically Active Agents A keratolytic agent may be included as an active agent of a foamable composition. The term "keratolytically active agent" as used herein includes a compound that loosens and removes the stratum corneum of the skin, or alters the structure of the keratin layers of skin. Keratolytically active agents are used in the treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another Class of Keratolytically Active Agents Includes Urea and Urea Derivatives. Retinoids Another group of active agents includes retinol, retinal, all trans retinoic acid and derivatives, isomers and analogs thereof, collectively termed "retinoids". Etretinate, actiretin, isotretinoin, adapalene and tazarotene are further examples of said retinoid isomers and analogs. Foamable compositions containing retinoids as the active drug can be used for the treatment of acne, seborrhea, various dermatoses, inflammation of the skin, mucosal membranes, vagina and the rectum, psoriasis, actinic keratosis and skin cancers, by application onto the affected area.

Insecticide and Insect Repellents Agents

Insects such as mosquitoes, biting flies, mites, gnats, fleas, chiggers, punkies, sand flies, lice and ticks can be annoying and sometimes pose a serious risk to human and animal health. In certain areas of the United States, mosquitoes can transmit diseases like equine and St. Louis encephalitis. Biting flies can inflict a painful bite that can persist for days, swell, and become infected. Ticks can transmit serious diseases like Lyme disease and Rocky Mountain spotted fever.

Insect repellents may be added to the foamable composition to protect people and animals from flying or biting insects, spiders, ticks and mites.

Examples of insect repellants include, but are not limited to, DEET (N,N-diethyl-m-toluamide), dimethyl phthalate, piperonyl butoxide and permethrin. Insect repelling terpenoids, have been reported by Hwang, et al, J. Chem. Ecol., 11, 1297 (1985); and Ruledge, J. Am. Mosquito Control Assoc. 4, 414 (1988).

A particular group of insect repellents includes the terpenoid compounds, described in U.S. Pat. No. 5,411,992, including:

(1) Terpenoid-alcohol or terpene-ols are terpenoids which have at least one hydroxyl group. Examples of terpene-ols include: C10H16O compounds, perillyl alcohol, carveol, myrtenol, and cis-verbenol; C10H18O compounds, myrtanol, iso-pinocampheol, dihydrocarveol, isopulegol, terpineol, terpinen-4-ol, nerol, geraniol, and linalool, and C10H20O compounds, menthol, beta-citronellol, and dihydro-myrcenol.

(2) Terpenoid-esters are terpenoids, which have at least one ester group which is the product of the bonding of the hydroxyl group of a terpene-ol with an aliphatic carboxylic acid that can contain functional groups such as the hydroxyl or amine on the aliphatic chain. Examples of suitable aliphatic carboxylic acids include acetic acid, propionic acid, lactic acid, and various amino acids. Examples of terpenoid-esters include: carvyl acetate, carvyl propionate, and menthyl lactate.

(3) Essential oils which contain terpenoids and perfumes which contain terpenoids. Non-limiting examples of essential oils having a high content of terpene-ols and esters include bergamot (62% terpenoids); sage (>50% terpenoids); *styrax* (>50% terpenoids); peppermint (>50% terpenoids); and pine Siberian (75% terpenoids %). Terpenes, aldehydes and ketones vary in their usefulness but as a general group have potential as insect-repellent.

The foamable composition is particularly suitable for the effective uniform spreading of an insect repellent agent onto large areas of the skin of humans and animals. The hydrophobic solvent present in the foam composition helps retain the insect repellent on the skin surface for an extended period of time.

The foamable composition is suitable for delivery of insect-killing agents (insecticides) to an afflicted external surface area of humans and animals. Thus, the pharmaceutical or cosmetic composition includes an insecticide selected from the group consisting of permethrin, hexachlorobenzene, carbamate, naturally occurring pyrethroids, permethrin, allethrin, malathion, piperonyl butoxide and any combination thereof at a therapeutically effective concentration. The application of the composition is very convenient and it spreads easily, even over hairy areas. The hydrophobic solvent present in the foam composition helps retain the insecticide on the treated area for an extended period of time. Furthermore, the presence of a hydrophobic solvent in the foam eases mechanical removal of lice and nits with a comb.

Anti-Cancer Drugs

Anti-cancer drugs can also be used as the drug of choice for the treatment of skin malignant tumors such as basal cell carcinoma, squamous cell carcinoma, melanoma and Kaposi's sarcoma, as well as the pre-cancerous condition actinic keratosis. In certain cases, topical cytotoxic and antiproliferative drugs are used to treat or prevent such cancers, including 5-fluorouracil, also called 5-FU. 5-FU, as well as any other anti-cancer agents, know in the art of cancer medicine, can be incorporated in the foam at therapeutically effective levels. An exemplary family of anticancer drugs, suitable for usage in the foam of the present formulation comprises antiestrogens, such as tamoxifen.

Photodynamic Therapy Agents

The foam composition is also useful to deliver photo-sensitizing agents. A photosensitizer can be selected from the group consisting of porphyrins, modified porphyrins, psoralen, 8-methoxypsoralen, 5-methoxypsoralen, psoralen derivatives, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives and photosensitizer precursors, such as aminolevulinic acid (ALA).

Active Agents for Burns, Wounds, Cuts and Ulcers

The treatment of burns, wounds, cuts and ulcers using a foamable composition is particularly advantageous. The foam can include both anti-infective agents (against bacteria, fungi and/or viruses), antiinflammatory agents (steroidal and/or NSAIDs) and pain relieving components. Upon application, the foam spreads easily, covering the surface of the affected area, and without causing pain.

Skin Care Active Agents

The foam composition is useful and advantageous for skin care and cosmetic care. The combination of oil and water having moisture-retaining properties in a spreadable foam form can be used to substitute currently used cosmetic skin care creams, lotions, gels, etc. The cosmetic foam compositions are suitable for the further application as "cosmeceutical" preparation (cosmetic products with therapeutic benefit), to treat "cosmetic" skin disorders, such as aging skin, wrinkles, hyperpigmentation (melasma, chloasma, freckles, etc.), scaly skin and other skin undesirable properties.

The CTFA Cosmetic Ingredient Handbook describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and humectants facilitating regulating the residence of an active agent in the skin), skin soothing and/or healing agents (e.g., panthenol and derivatives (e.g., ethyl panthenol), aloe vera, pantothenic acid and pantothenic acid derivatives, allantoin, bisabolol, and dipotassium glycyrrhizinate), skin treating agents, thickeners, and vitamins and derivatives thereof.

Anti-Acne Active Agents

An anti-acne agent can be included in the foamable composition. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration.

Anti-Wrinkle Active Agents/Anti-Atrophy Active Agents and Agents to Treat Dry and Scaly Skin (Xerosis and Ichthyosis)

The foamable composition may also include an effective amount of an anti-wrinkle active and/or at least one anti-atrophy active. Exemplary anti-wrinkle/anti-atrophy active agents suitable for use in the foamable compositions include sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

Anti-Oxidants/Radical Scavengers

An effective amount of an anti-oxidant/radical scavenger can be added to the foamable compositions, for example, in an amount from about 0.1% to about 10% (w/w), or from about 1% to about 5% (w/w).

Anti-oxidants/radical scavengers such as ascorbic acid (vitamin C) and ascorbic acid salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox.®), gallic acid and gallic acid alkyl esters, especially propyl gallate, uric acid and uric acid salts and alkyl esters, sorbic acid and sorbic acid salts, lipoic acid, amines (e.g., N,N-diethylhydroxylamine, amino-guanidine), sulfhydryl compounds (e.g., glutathione), dihydroxy fumaric acid and dihydroxy fumaric acid salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts can be used.

The foam is suitable for delivering skin protecting and revitalizing anti-oxidants/radical scavengers. Polyunsaturated fatty acids containing omega-3 and omega-6 fatty acids (e.g., linoleic and linolenic acid, gamma-linoleic acid (GLA), eicosapentaenoic acid (EPA) and docosahexaenoic acid (DHA)) are beneficial in the treatment of psoriasis and other skin inflammation conditions. Likewise, emollients and silicone oils exert moisture-retaining and skin protective effects on the skin. Thus, a skin protective foam is provided, wherein the hydrophobic solvent comprises in full or in part, a solvent, selected from the group of emollients, silicone oil and oils, rich in unsaturated fatty acids, thus, affording a synergistic therapeutic effect of the anti-oxidants/radical scavenger agent and the vehicle components.

Self-Tanning Active Agents

The foam composition is particularly suitable for the uniform delivery of a tanning active agent onto large areas of the skin. The compositions contain from about 0.1% to about 20%, or from about 2% to about 7%, or even from about 3% to about 6% of dihydroxyacetone or any other compound know in the art as an artificial tanning active agent.

Skin Lightening and Whitening Agents

The foam composition may be formulated to provide a composition for the uniform delivery of a skin lightening agent. When used, the composition contains from about 0.1% to about 10%, or from about 0.2% to about 5% of a skin-lightening agent. Suitable skin lightening or whitening agents include those known in the art, including hydroquinone, azelaic acid and other related dicarboxylic acids, and salts and derivatives thereof, retinoids, kojic acid, arbutin, nicotinic acid and nicotinic acid precursors, salts and derivatives, ascorbic acid and salts and derivatives thereof (e.g., magnesium ascorbyl phosphate or sodium ascorbyl phosphate), and herbal extracts (e.g., mulberry extract, placental extract).

In one or more embodiments of the present invention, the foam composition includes a combination of at least one skin-whitening agent and at least one additional active agent selected from retinoids, keratolytically active agents and anti-inflammatory agents.

In one or more embodiments, the composition includes a combination of at least one skin-whitening agent and at least one keratolytically active agent selected from a alpha-hydroxy acids, beta hydroxy acids, and retinoids.

In one or more embodiments of the present invention, the foam composition includes a combination of a skin-whitening agent and an inorganic sunscreen agent. When inorganic sunscreen agents, e.g. titanium dioxide and zinc oxide, are rubbed onto the skin, they leave a white coating, which provides an instant (although transient) whitening effect, which is highly desirable by the consumer, who wishes to see instant change in his/her appearance. The whitening agent, in combination with the inorganic sunscreen agent in the foam carrier can be easily and uniformly distributed on the skin surface, thereby affording an even instant whitening effect, unlike creams that are difficult to spread evenly on skin areas.

Agents for Hair Growth Disorders

[Agents that affect the pattern of hair growth can be suitably incorporated in the foam composition. Male pattern baldness (MPB), the commonest cause of balding, is induced by the activity of the male hormone dihydrotestosterone (DHT), which is converted from the hormone testosterone by the enzymes 5-alpha reductase. Current treatments of MPB include minoxidil and agents, which inhibit 5-alpha reductase, such as finasteride, spironolactone, azelaic acid and azelaic acid derivatives and salts. Such agents, as well as other agents known in the art, can be incorporated in the foam composition.

Polyunsaturated fatty acids, i.e., such which include any of the essential fatty acids (EFA's), such as linoleic and linolenic acid, gamma-linoleic acid (GLA), eicosapentaenoic acid (EPA) and docosahexaenoic acid (DHA), are also known to contribute to hair growth. Thus, a hair growth foam composition is provided, in which the hydrophobic solvent comprises in full or in part, an oil, rich in such unsaturated fatty acids.

Figure-forming Agents; Agents to Treat Cellulite/Slimming

Figure forming agents such as used in the treatment of cellulite and in slimming products can be suitably incorporated in the foam composition. A non-limiting exemplary list of active agents known in the treatment of cellulite and in the induction of a slimming effect include:

- Herbal extracts: baldderwack extract, butcher's, broom, cayenne, dandelion, red clover, *ginkgo biloba*, horse chestnut, witch hazel and borage oil
- Omega 3 and omega 6 oils
- Caffeic acid and salts and derivatives thereof
- Xanthine agents, such as theophiline and pentoxyphilline
- Nicotinic acid and salts and derivatives thereof.

Agents to Treat Sunburn, Heat Burn, Radiation Burn, Rash and Itch

Cosmetic and pharmaceutical ingredients which are known in the art of pharmacology and cosmetology to treat dermatitis, minor skin irritations, sunburn, heat burn, radiation burn, and inhibit inflammation can be beneficially incorporated in the foam composition.

Examples of such active agents include chamomile extract (*matricaria recutitia*), cucumber distillate (*cucumis sativus*), lavender water (*lavendula angustifolia*), rose water (*rosa damascena*), witch hazel (*hamamelis virginiana*), allantoin, bisabolol, rosehip oil, *calendula* oil, azulaene, menthol and camphor.

Other Skin Care Active Agents

The active agent can be selected from the group of sulfur-containing amino acids, thiol compounds, alpha hydroxy acids, lactic acid and lactic acid derivatives and salts, glycolic acid, glycolic acid derivatives and glycolic acid salts, beta-hydroxy acids, salicylic acid and salicylic acid salts and derivatives, phytic acid, lipoic acid, lysophosphatidic acid, skin peel agents, phenol, resorcinol, vitamin B3 compounds, niacinamide, nicotinic acid and nicotinic acid salts and esters, tocopheryl nicotinate, nicotinyl amino acids, nicotinyl alcohol esters of carboxylic acids, nicotinic acid N-oxide and niacinamide N-oxide, retinoids, retinol, retinal, retinoic acid, retinyl acetate, retinyl palmitate and retinyl ascorbate, caffeine, theophilline, pentoxyphilline, dihydroxy acetone kojic acid, arbutin, nicotinic acid and nicotinic acid precursors, nicotinic acid salts, nicotinic acid derivatives, ascorbic acid, ascorbic acid salts and ascorbic acid derivatives "Alcohol Free"

The foam carrier or foam composition is essentially free of short chain aliphatic alcohols (i.e., methyl, ethyl, isopropyl and butyl alcohol), unlike the composition disclosed in U.S. Pat. Nos. 6,126,920 and 6,358,541, which contains an aliphatic alcohol, preferably in amounts of 40-90% aliphatic alcohol. For the purpose of the present application, the term "alcohol free" refers to compositions that contain no more than 7.5% by weight of any aliphatic alcohol, having one to six carbon atoms in their carbon backbone, or no more than 7.5% by weight of any mixture of such aliphatic alcohols.

Optional Ingredients

The pharmaceutical or cosmetic foam carrier optionally includes a variety of pharmaceutical or cosmetic ingredients, which are added in order to fine-tune the consistency of the formulation, protect the formulation components from degradation and oxidation and bestow their cosmetic acceptability. Such an excipient is preferably selected from the group consisting of: a diglyceride, a triglyceride, a stabilizing agent, an antioxidant, glycerol, a flavoring, a colorant, an odorant agent and any other formulation component known in the art of pharmaceutical and cosmetic formulary. A pharmaceutical or cosmetic composition manufactured using the foam carrier according to the present invention is very easy to use. When applied onto the afflicted body surface of humans or animals, it is in a foam state, allowing free application without spillage. Upon further application of a mechanical force, e.g., by rubbing the composition onto the body surface, it freely spreads on the surface and is rapidly absorbed.

Composition and Foam Physical Characteristics

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition or carrier includes water, hydrophobic solvents, surfactant, gelling agent and propellant, thereby creating a stable emulsion having an acceptable shelf-life of at least one year, or at least two years at ambient temperature. A feature of a product for cosmetic or medical use is long term stability. Propellants, which are a mixture of low molecular weight hydrocarbons, tend to impair the stability of emulsions. It has been observed, however, that foam compositions including amphiphilic copolymers as gelling agents are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

A further aspect of the foam is breakability. The breakable foam is thermally stable, yet breaks under sheer force. Sheer-force breakability of the foam is clearly advantageous over thermally-induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of between about 0.01 g/mL and about 0.1 g/mL.

Further Technical Parameters

The composition of the present invention can be contained in and dispensed from a container capable of withstanding the pressure of the propellant gas and having an appropriate valve/nozzle for dispensing the composition as foam under pressure. A customary liquefied propellant can be added, in the amount of about 3-18% of the total composition. Liquefied propellants are gases that exist as liquids under pressure, including high purity hydrocarbons such as propane, isobutane and n-butane, dimethyl ether and chlorofluorocarbons (CFCs).

A specific embodiment according to the present invention comprises placing the composition of the present invention on a patch, regulating residence of an active ingredient in the skin tape or the skin-contact compartment of a transdermal delivery apparatus and applying such object onto the skin, in order to attain effective superficial treatment or enhanced penetration of the drug into the skin or through the skin.

Utilizing such strategy, one can apply drugs, which are currently administered systemically or that require transdermal delivery, in the preferred therapeutic system of the present invention. Examples for such drugs are nicotine, testosterone and other male hormones and male hormone precursors, estrogen and other female hormones and hormone precursors, growth hormone, insulin, caffeine, steroidal and non-steroidal antiinflammatory agents and thyroid hormone substitutes.

The general process, as typically exemplified in Example 1 can be applied in order to produce the composition of the present invention.

The pharmaceutical carrier according to the present invention can also be used to prepare cosmetics for beauty purpose by adding into skin care agents and perfume.

Fields of Pharmaceutical Applications

By including an appropriate active component and optionally an appropriate at least one active agent, the foam composition of the present invention is useful in the therapy of a variety of disorders, such as classified, in a non-limiting exemplary manner, according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash; bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma; fungal infections including dermatophyte infections, yeast infections; parasitic infections including scabies, pediculosis, creeping eruption; viral infections; disorders of hair follicles and sebaceous glands including acne, rosacea, perioral dermatitis, hypertrichosis (hirsutism), alopecia, including male pattern baldness, alopecia greata, alopecia universalis and alopecia totalis; pseudofolliculitis barbae, keratinous cyst; scaling papular diseases including psoriasis, pityriasis rosea, lichen planus, pityriasis rubra pilaris; benign tumors including moles, dysplastic nevi, skin tags, lipomas, angiomas, pyogenic granuloma, seborrheic keratoses, dermatofibroma, keratoacanthoma, keloid; malignant tumors including basal cell carcinoma, squamous cell carcinoma, malignant melanoma, paget's disease of the nipples, Kaposi's sarcoma; reactions to sunlight including sunburn, chronic effects of sunlight, photosensitivity; bullous diseases including pemphigus, bullous pemphigoid, dermatitis herpetiformis, linear immunoglobulin A disease; pigmentation disorders including hypopigmentation such as vitiligo, albinism and postinflammatory hypopigmentation and hyperpigmentation such as melasma (chloasma), drug-induced hyperpigmentation, postinflammatory hyperpigmentation; disorders of cornification including ichthyosis, keratosis pilaris, calluses and corns, actinic keratosis; pressure sores; disorders of sweating; inflammatory reactions including drug eruptions, toxic epidermal necrolysis; erythema multiforme, erythema nodosum, granuloma annulare.

The foam composition is useful in the therapy of non-dermatological disorders, which respond to topical/transdermal delivery of an active agent. By way of example, such disorders include localized pain in general, as well as joint pain, muscle pain, back pain, rheumatic pain, arthritis, ostheoarthritis and acute soft tissue injuries and sports injuries. Other disorders of this class include conditions, which respond to hormone therapy, such as hormone replacement therapy, transdermal nicotine administration, and other respective disorders, known in the art of drug delivery.

The foam compositions are further useful for the treatment and prevention of disorders and diseases of other body cavities including the rectum, vagina, penile urethra and ear canal.

Thus, the foam compositions are useful in treating a patient having any one of a variety of gynecological disorders, such as classified, in a non-limiting exemplary manner, according to the following groups: pelvic pain, including premenstrual syndrome (PMS), mittelschmerz (severe midcycle pain due to ovulation), dysmenorrhea (pain related to the menstrual cycle), endometriosis, ectopic pregnancy, ovarian cysts and masses, acute pelvic inflammatory disease, pelvic congestion syndrome and vulvodynia; vulvovaginal infections, including bacterial vaginosis, candidal vaginitis, trichomonas vaginalis, herpes simplex genital ulcers and warts, pelvic inflammatory disease (PID), cervicitis, acute and chronic salpingitis; endometriosis; gynecological neoplasms, including endometrial Cancer, ovarian cancer, cervical cancer, vulvar cancer, vaginal cancer, fallopian tube cancer and gestational trophoblastic disease; benign tumors; sexually transmitted diseases; sexual dysfunction disorders that respond to pharmacological therapy, including sexual arousal disorder, female orgasmic disorder, dyspareunia and vaginismus; and various gynecological disorders that respond to hormonal therapy.

Rectal applications include, for example, anal abscess/fistula, anal cancer, anal warts, Crohn's disease, haemorrhoids, anal and perianal pruritus, soreness, and excoriation, perianal thrush, anal fissures, fecal incontinence, constipation, polyps of the colon and rectum.

The foam compositions are further useful for intra-vaginal and rectal treatment of sexually-transmitted and non-sexually-transmitted infectious disease (STDs).

In one or more embodiments, the invention provides a method of treatment of a disorder of the skin, mucosal membrane, ear channel, vaginal, rectal and penile urethra disorders, comprising topical application of the foam composition, whereby one or more active agents, in a therapeutically effective concentration to the afflicted area.

In a further embodiment, the invention provides a method of treatment of a non-dermatological disorder, which responds to topical delivery of an active agent, comprising topical application of the foam composition of the present invention, whereby one or more active agents, in a therapeutically effective concentration to the skin.

Treatment/Therapy

The terms "therapy" and "treatment" as used herein interchangeably, cover any treatment of a disease or disorder, and includes, for example:

(i) Curing the disease or disorder;
(ii) preventing the disease or disorder from occurring in a subject which may be predisposed to the disease but has not yet been diagnosed as having it;
(iii) inhibiting the disease or disorder;
(iv) relieving the disease or disorder;
(iv) causing regression of the disease;
(v) providing a beneficial immunological effect;
(vi) improving the quality of life of a subject afflicted by a disease or disorder; and, in the case of cosmetic treatment (vii) cleansing, beautifying, promoting attractiveness, or altering the appearance without affecting the body's structure or functions

EXAMPLES

In the following, we are going to describe some examples and experiments in detail. This invention is not limited to these examples and experiments. Many variations will suggest themselves are within the full intended scope of the appended claims.

Example 1

Production of Pharmaceutical or Cosmetic Foam Carrier and Composition—General Method The method for preparing of a pharmaceutical foam carrier generally comprised following steps.

Step 1—Aqueous Phase: Gelling agent and surface-active agent are dissolved in water, with agitation. The solution is warmed to 50-70° C. Water soluble cosmetic or pharmaceutical active Ingredients* and optional water soluble ingredients are added with agitation to the Aqueous Phase mixture.

Step 2—Hydrophobic Phase: The hydrophobic solvent is heated to same temperature. Oil soluble cosmetic or pharmaceutical active agents* and optional oil soluble formulation ingredients are added with agitation to the Hydrophobic Phase mixture.

Step 3—The warm Hydrophobic Phase is gradually poured into the warm Aqueous Phase, with agitation, followed by Ultraturax homogenization. The mixture is allowed to cool down to ambient temperature.

Step 4—The mixture, at ambient temperature, is added to an aerosol container, the container is sealed and appropriate amount of propellant (about 10% of the composition mass) is compressed into the container.

In case of heat sensitive active ingredients, add the active ingredient with agitation to the mixture, after Step 3.

In the following examples, foam compositions were prepared as described above and tested for foam quality

Example 2

Diclofenac Foam Composition with Transcutol

| Component | % w/w |
|---|---|
| Mineral oil (hydrophobic solvent) | 6.00 |
| Isopropyl myristate (hydrophobic solvent) | 6.00 |
| Stearyl alcohol (foam adjuvant) | 1.00 |
| Xanthan gum (gelling agent) | 0.30 |
| Methocel K100M (gelling agent) | 0.30 |
| TWEEN 80 (surfactant) | 1.00 |
| MYRJ 49p (surfactant) | 3.00 |
| Cocamidopropyl betaine (surfactant) | 0.50 |
| Transcutol p (therapeutic enhancer) | 20.00 |
| Glyceryl monostearate (co-emulsifier) | 0.50 |
| Diclofenac sodium (active agent) | 1.00 |
| Phenonip (preservative) | 0.30 |
| Butane/propane (propellant) | 8.00 |
| Water | to 100.0 |
| Foam Quality | E |
| Density | 0.028 |

Example 3

Local Anesthetic Lidocaine Foam Compositions with Either Urea, Lactic Acid or a Therapeutic Enhancer

| Component | % w/w | | | | |
|---|---|---|---|---|---|
| Mineral oil | 6.00 | 6.00 | 6.00 | 6.00 | 12.00 |
| Isopropyl myristate | 6.00 | 6.00 | 6.00 | 6.00 | 12.00 |
| Glyceryl monostearate | 0.50 | 0.50 | 0.50 | 0.50 | 1.00 |
| Stearyl alcohol | 1.00 | 1.00 | 1.00 | 1.00 | 1.00 |
| Xanthan gum | 0.30 | 0.30 | 0.30 | 0.30 | 0.30 |
| Methocel K100M | 0.30 | 0.30 | 0.30 | 0.30 | 0.30 |
| TWEEN 60 | 1.00 | | | | |
| TWEEN 80 | | 1.00 | 1.00 | 1.00 | 2.00 |
| MYRJ 49p | 3.00 | 3.00 | 3.00 | 3.00 | 4.00 |
| Lactic acid | 10.00 | 5.00 | | | |
| Glycofurol | | | 1.00 | 10.00 | |
| Urea | | | | | 10.00 |
| Cocamidopropyl betaine | — | 0.50 | — | 0.50 | — |
| Lidocaine base | 4.00 | 4.00 | 4.00 | 4.00 | 4.00 |
| Phenonip | 0.30 | 0.30 | 0.30 | 0.30 | 0.30 |
| Butane/propane | 8 | 8 | 6 | 10 | 10 |
| Water | to 100 | to 100 | to 100 | to 100 | to 100 |
| Foam Quality | E | E | E | E | E |
| Density | 0.028 | 0.038 | 0.044 | 0.028 | 0.028 |
| Mineral oil | 6.00 | 6.00 | 6.00 | 22.00 | 6.00 |
| Isopropyl myristate | 6.00 | 6.00 | 6.00 | 22.00 | 6.00 |
| Glyceryl monostearate | 0.50 | 0.50 | 0.50 | 1.00 | 0.50 |
| Stearyl alcohol | 1.00 | 1.00 | 1.00 | 1.00 | 1.00 |
| Xanthan gum | 0.30 | 0.30 | 0.30 | 0.40 | 0.30 |
| Methocel K100M | 0.30 | 0.30 | 0.30 | 0.40 | 0.30 |
| TWEEN 80 | | 1.00 | 1.00 | 2.00 | 1.00 |
| MYRJ 49p | 1.00 | 3.00 | 3.00 | 4.00 | 3.00 |
| Propylene glycol | 3.00 | | | | |
| Transcutol p | | 10.00 | 1.00 | 2.00 | 10.00 |
| Cocamidopropyl betaine | 0.50 | 0.50 | 0.50 | 0.50 | 0.50 |
| Lidocaine base | 4.00 | 4.00 | 4.00 | 4.00 | 4.00 |
| Phenonip | 0.30 | 0.30 | 0.30 | 0.30 | 0.30 |
| Butane/propane | 8 | 8 | 6 | 8 | 10 |
| Water | to 100 | to 100 | to 100 | to 100 | to 100 |
| Foam Quality | E | E | E | E | E |
| Density | 0.032 | 0.035 | 0.048 | 0.075 | 0.025 |

Example 4

Foam Compositions with Urea

| Component | % w/w | | | |
|---|---|---|---|---|
| Mineral oil | 6.00 | 6.00 | 6.00 | 6.00 |
| Isopropyl myristate | 6.00 | 6.00 | 6.00 | 6.00 |
| Glyceryl monostearate | 0.50 | 0.50 | 0.50 | 0.50 |
| Stearyl alcohol | 0.20 | 0.20 | 0.20 | 1.00 |
| Urea | 10.00 | 10.00 | 10.00 | 10.00 |
| Xanthan gum | 0.30 | 0.30 | 0.30 | 0.30 |
| Methocel K100M | 0.30 | 0.30 | 0.30 | 0.30 |
| Myrj 52 | | | | 3.00 |
| TWEEN 80 | | | | 1.00 |
| Myrj 49p | | | 3.00 | |
| TWEEN 60 | 1.00 | 1.00 | 1.00 | |
| Cocamidopropyl betaine | 0.50 | 0.50 | 0.50 | |
| Phenonip | 0.30 | 0.30 | 0.30 | 0.30 |
| Butane/propane | 8.00 | 8.00 | 8.00 | 6.00 |
| Water | to 100 | to 100 | to 100 | to 100 |
| Foam Quality | E | E | E | E |
| Density | n/a | 0.023 | n/a | 0.044 |
| Mineral oil | 6.00 | | 6.00 | |
| Isopropyl myristate | 6.00 | | 6.00 | |
| Glyceryl monostearate | 0.50 | | 0.50 | |
| Stearyl alcohol | 1.00 | | 1.00 | |
| Urea | 40.00 | 40.00 | 20.00 | 20.00 |
| Xanthan gum | 0.30 | 0.30 | 0.30 | 0.30 |
| Methocel K100M | 0.30 | 0.30 | 0.30 | 0.30 |
| Myrj 52 | 3.00 | 3.00 | 3.00 | 3.00 |
| TWEEN 80 | 1.00 | 1.00 | 1.00 | 1.00 |
| Cocamidopropyl betaine | 0.50 | 0.50 | | 0.50 |
| Phenonip | 0.30 | 0.30 | 0.30 | 0.30 |
| Butane/propane | 8.00 | 6.00 | 8.00 | 8.00 |
| Water | to 100 | to 100 | to 100 | to 100 |
| Foam Quality | E | E | E | E |
| Density | 0.022 | 0.029 | 0.032 | 0.024 |

| Component | % w/w |
|---|---|
| Capric/caprylic triglycerides | 12.00 |
| Glyceryl monostearate | 0.50 |
| Tween 80 | 3.0 |
| Pemulene TR1 | 0.50 |
| Hydrophilic Drug | 1.0 |
| Urea | 10.0 |
| Phenonip | 0.30 |
| Butane/propane | 8.00 |
| Water | to 100 |
| Foam Quality | E |
| Density | 0.030 |
| Capric/caprylic triglycerides | 12.00 |
| Glyceryl monostearate | 0.50 |
| Tween 80 | 3.0 |
| Pemulene TR1 | 0.50 |
| Hydrophobic Drug | 1.0 |
| Urea | 10.0 |
| Phenonip | 0.30 |
| Butane/propane | 8.00 |
| Water | to 100 |
| Foam Quality | E |
| Density | 0.030 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Urea | 10.00 |
| Cocamidopropyl betaine | 0.50 |
| Hydrophilic Drug | 0.1-2.0 |
| Phenonip | 0.30 |
| Butane/propane | 6.00 |
| Water | to 100 |
| Foam Quality | E |
| Density | 0.034 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Urea | 10.00 |
| Cocamidopropyl betaine | 0.50 |
| Lipophilic Drug | 2.0 |
| Phenonip | 0.30 |
| Butane/propane | 8.00 |
| Water | to 100 |
| Foam Quality | E |
| Density | 0.020 |
| Capric/caprylic triglycerides | 12.00 |
| Glyceryl monostearate | 0.50 |
| Pemulene TR1 | 0.50 |
| Methocel K100M | 0.30 |
| Xanthan gum | 0.30 |
| Urea | 10.00 |
| Ketoconazole | 1.0 |
| Phenonip | 0.30 |
| Butane/propane | 8.00 |
| Water | to 100 |
| Foam Quality | E |
| Density | 0.020 |

Example 5

Further Foam Composition with Either Transcutol or Glycofurol

| Component | % w/w |
|---|---|
| Isopropyl myristate | 30.00 |
| Glyceryl monostearate | 0.50 |
| Xanthan gum | 0.30 |
| Methocel K100M | 0.30 |
| TWEEN 80 | 1.00 |
| MYRJ 49p | 3.00 |
| Cocamidopropyl betaine | 0.50 |
| Transcutol p | 20.00 |
| Hyrdophylic drug | 1.0 |
| Phenonip | 0.30 |
| Butane/propane | 8.00 |
| Water | to 100 |
| Foam Quality | E |
| Density | 0.028 |
| Isopropyl myristate | 30.00 |
| Glyceryl monostearate | 0.50 |
| Xanthan gum | 0.30 |
| Methocel K100M | 0.30 |
| TWEEN 80 | 1.00 |
| MYRJ 49p | 3.00 |
| Cocamidopropyl betaine | 0.50 |
| Transcutol p | 20.00 |
| Hyrdophobic drug | 1.0 |
| Phenonip | 0.30 |
| Water | to 100 |
| Butane/propane | 8.00 |
| Foam Quality | E |
| Density | 0.030 |
| Capric/caprylic triglycerides | 12.00 |
| Glyceryl monostearate | 0.50 |
| Pemulene TR1 | 0.50 |
| Methocel K100M | 0.30 |
| Xanthan gum | 0.30 |
| Transcutol | 10.00 |
| Ketoconazole | 1.0 |
| Phenonip | 0.30 |
| Water | to 100 |

-continued

| Component | % w/w |
|---|---|
| Butane/propane | 8.00 |
| Foam Quality | E |
| Density | 0.038 |
| Capric/caprylic triglycerides | 12.00 |
| Glyceryl monostearate | 0.50 |
| Pemulene TR1 | 0.50 |
| Methocel K100M | 0.30 |
| Xanthan gum | 0.30 |
| Glycofurol | 10.00 |
| Ketoconazole | 1.0 |
| Phenonip | 0.30 |
| Water | to 100 |
| Butane/propane | 8.00 |
| Foam Quality | E |
| Density | 0.034 |

Example 6

Foam Compositions with Hydroxy Acids

| Component | % w/w |
|---|---|
| Capric/caprylic triglycerides | 18.00 |
| Glyceryl monostearate | 0.50 |
| Pemulene TR1 | 0.50 |
| Methocel K100M | 0.30 |
| Xanthan gum | 0.30 |
| Hydrophilic Drug | 1.0 |
| Lactic acid | 6.0 |
| Phenonip | 0.30 |
| Butane/propane | 8.00 |
| Water | to 100 |
| Foam Quality | E |
| Density | 0.030 |
| Capric/caprylic triglycerides | 18.00 |
| Glyceryl monostearate | 0.50 |
| Pemulene TR1 | 0.50 |
| Methocel K100M | 0.30 |
| Xanthan gum | 0.30 |
| Hydrophobic Drug | 1.0 |
| Lactic acid | 6.0 |
| Phenonip | 0.30 |
| Butane/propane | 6.00 |
| Water | to 100 |
| Foam Quality | E |
| Density | 0.038 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Glycolic acid | 4.00 |
| Cocamidopropylbetaine | 0.50 |
| Hydrophilic Drug | 2.0 |
| Phenonip | 0.30 |
| Butane/propane | 6.00 |
| Water | to 100 |
| Foam Quality | E |
| Density | 0.044 |
| Capric/caprylic triglycerides | 25.00 |
| Glyceryl monostearate | 0.50 |
| Stearyl alcohol | 1.00 |
| Xanthan gum | 0.30 |
| Methocel K100M | 0.30 |
| TWEEN 80 | 1.00 |
| MYRJ 52P | 3.00 |
| Glycolic acid | 4.00 |
| Cocamidopropylbetaine | 0.50 |

-continued

| Component | % w/w |
|---|---|
| Hydrohobic Drug | 2.0 |
| Phenonip | 0.30 |
| Butane/propane | 12.00 |
| Water | to 100 |
| Foam Quality | E |
| Density | 0.020 |

Although various embodiments that incorporate the teachings of the present invention have been shown and described in detail herein, those skilled in the art can readily devise many other varied embodiments that incorporate these teachings.

The invention claimed is:

1. A foamable composition comprising:
 (i) about 0.1 to 5% by weight of a surface-active agent selected from the group consisting of a polysorbate, a polyoxyethylene fatty acid ester, a polyoxyethylene alkyl ether, a sucrose ester, a partial ester of sorbitol, a partial ester of sorbitol anhydride, sodium methyl cocoyl taurate, sodium methyl oleoyl taurate, sodium lauryl sulfate, triethanolamine lauryl sulfate, a betaine, a mono-, di- or tri-ester of sucrose with food fatty acids (sucrose esters), a monoglyceride, a diglyceride, polyoxyethylene (20) sorbitan monostearate, polyoxyethylene (20) sorbitan monooleate, Myrj 45 (Polyoxyethylene (8) Stearate), Myrj 49 (polyoxyethylene (20) stearate), Myrj 59 (polyoxyethylene (100) stearate), a polyoxyethylene cetyl ether, a polyoxyethylene palmityl ether, a polyethylene oxide hexadecyl ether, Brij 52 (polyoxyethylene (2) cetyl ether), Brij 56 (polyoxyethylene (10) cetyl ether), sorbitan monolaurate, isoceteth-20, cocamidopropyl betaine, and Myrj 52 (polyoxyethylene 40 stearate);
 (ii) about 0.1 to 5% by weight of a gelling agent;
 (iii) an active component selected from the group consisting of one or more of urea and a hydroxy acid;
 (iv) water; and
 (v) a liquefied or a compressed gas propellant at a concentration of about 3% to about 18% by weight of the total composition;
 wherein the composition contains no more than 7.5% of methyl alcohol, ethyl alcohol, isopropyl alcohol, butyl alcohol, or mixtures thereof;
 and wherein the composition forms a breakable foam upon dispensing.

2. The foamable composition of claim 1, further comprising about 5 to about 50% by weight of composition of a liquid, non-volatile hydrophobic solvent, wherein said composition is an oil in water emulsion.

3. The foamable emulsion of claim 2, wherein said emulsion is stable in its pre-dispensed state.

4. The foamable composition of claim 1, wherein said active component consists of about 1% to about 50% urea.

5. The foamable composition of claim 4, wherein said active component consists of about 10% to about 20% urea.

6. The foamable composition of claim 4, wherein said active component consists of about 20% to about 50% urea.

7. The foamable composition of claim 1, wherein said active component consists of about 1% to about 30% hydroxy acid.

8. The foamable composition of claim 7, wherein said active component consists of about 1% to about 10% hydroxy acid.

9. The foamable composition of claim 7, wherein said active component consists of about 10% to about 30% hydroxy acid.

10. The foamable composition of claim 1, wherein said active component consists of a combination of about 1% to about 50% urea and about 1% to about 30% hydroxy acid.

11. An oil in water foamable composition comprising:
(i) about 5 to about 50% by weight of composition of a liquid, non-volatile hydrophobic solvent;
(ii) about 0.1 to 5% by weight of a surface-active agent selected from the group consisting of a polysorbate, a polyoxyethylene fatty acid ester, a polyoxyethylene alkyl ether, a sucrose ester, a partial ester of sorbitol, a partial ester of sorbitol anhydride, sodium methyl cocoyl taurate, sodium methyl oleoyl taurate, sodium lauryl sulfate, triethanolamine lauryl sulfate, a betaine, a mono-, di- or tri-ester of sucrose with food fatty acids (sucrose esters), a monoglyceride, a diglyceride, polyoxyethylene (20) sorbitan monostearate, polyoxyethylene (20) sorbitan monooleate, Myrj 45 (Polyoxyethylene (8) Stearate), Myrj 49 (polyoxyethylene (20) stearate), Myrj 59 (polyoxyethylene (100) stearate), a polyoxyethylene cetyl ether, a polyoxyethylene palmityl ether, a polyethylene oxide hexadecyl ether, Brij 52 (polyoxyethylene (2) cetyl ether), Brij 56 (polyoxyethylene (10) cetyl ether), sorbitan monolaurate, isoceteth-20, cocamidopropyl betaine, and Myri 52 (polyoxyethylene 40 stearate);
(iii) about 0.1 to 5% by weight of a gelling agent;
(iv) a therapeutic enhancer selected from the group consisting of propylene glycol, butylene glycols, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and cyclodextrins; and
a liquefied or compressed gas propellant at a concentration of about 3% to about 18% by weight of the total composition;
wherein the composition contains no more than 7.5% of methyl alcohol, ethyl alcohol, isopropyl alcohol, butyl alcohol, or mixtures thereof; and
wherein said composition is a stable emulsion in its pre-dispensed state and forms a breakable foam upon dispensing.

12. The foamable composition of claim 11, wherein the composition comprises about 1% to about 10% of the therapeutic enhancer.

13. The foamable composition of claim 11, wherein the composition comprises about 10% to about 30% of the therapeutic enhancer.

14. The foamable composition of claim 1, 2, 4, 7 or 11, further comprising a therapeutically effective concentration of at least one active agent.

15. The foamable composition of claim 2 or 11, wherein said hydrophobic solvent comprises about 5-10% by weight of the composition.

16. The foamable composition of claim 2 or 11, wherein said hydrophobic solvent comprises about 10-20% by weight of the composition.

17. The foamable composition of claim 2 or 11, wherein said hydrophobic solvent comprises about 20-50% by weight of the composition.

18. The foamable composition of claim 2 or 11, wherein said hydrophobic solvent comprises a mixture of mineral oil and an emollient in a ratio between 2:8 and 8:2 on a weight basis.

19. The foamable composition of claim 1 or 11, wherein said surface-active agent is selected from the group consisting of a non ionic surface active agent, a cationic surface active agent, an amphoteric surface active agent and a zwitterionic surface active agent.

20. The foamable composition of claim 1 or 11, wherein said surface-active agent is a mixture of a non ionic surface active agent and an ionic surface active agent in a 1:1 to 20:1 ratio.

21. The foamable composition of claim 1 or 11, wherein said surface-active agent is a non ionic surface-active agent.

22. The foamable composition of claim 1 or 11, wherein the surface-active agent has HLB value of more than 9.

23. The foamable composition of claim 1 or 11, wherein the gelling agent comprises an amphiphilic copolymer.

24. The foamable composition of claim 2 or 11, wherein the hydrophobic solvent is selected from the group consisting of vegetable oil, marine oil, mineral oil, emollient, silicone oil, plant-derived therapeutic oil and mixture thereof at any proportion.

25. The foamable composition of claim 2 or 11, wherein the ratio between the surface active agent and the hydrophobic solvent is between about 1:8 and about 1:16.

26. The foamable composition of claim 2 or 11, wherein the ratio between the surface active agent and the hydrophobic solvent is between about 1:16 and about 1:32.

27. The foamable composition of claim 14, wherein said active agent is antibacterial.

28. The foamable composition of claim 27, wherein said active agent is selected from the group consisting of chloramphenicol, tetracyclines, synthetic and semi-synthetic penicillins, beta-lactams, quinolones, fluoroquinolnes, macrolide antibiotics, peptide antibiotics, cyclosporines, Metronidazole, free radical generating agents, iodine, chlorhexidine, benzoyl peroxide, hydrogen peroxide and any combination thereof at a therapeutically effective concentration.

29. The foamable composition of claim 14, wherein said active agent is antifungal.

30. The foamable composition of claim 29, wherein said active agent is selected from the group of azoles, diazoles, triazoles, miconazole, fluconazole, ketoconazole, clotrimazole, itraconazole griseofulvin, ciclopirox, amorolfine, terbinafine, amphotericin B, potassium iodide, flucytosine (5FC) and any combination thereof at a therapeutically effective concentration.

31. The foamable composition of claim 14, wherein said active agent is antiviral.

32. The foamable composition of claim 31, wherein said active agent is selected from the group consisting of vidarabine, acyclovir, gancyclovir, nucleoside-analog reverse transcriptase inhibitors, AZT (zidovudine), ddI (didanosine), ddC (zalcitabine), d4T (stavudine), 3TC (lamivudine), non-nucleoside reverse transcriptase inhibitors, nevirapine, delavirdine, protease Inhibitors, saquinavir, ritonavir, indinavir, nelfinavir, ribavirin, amantadine, rimantadine and interferon.

33. The foamable composition of claim 14, wherein said active agent is selected from the group consisting of an anti-inflammatory agent and an anti-allergic agent.

34. The foamable composition of claim 33, wherein said active agent is selected from the group comprising corticosteroids, non-steroidal antiinflammatory drugs, anti- histamines, immunomodulating agents, immunosuppressants and any combination thereof at a therapeutically effective concentration.

35. The foamable composition of claim 33 wherein the anti-inflammatory agent is selected from the group comprising clobetasol proprionate, halobetasol proprionate, betamethasone diproprionate, betamethasone valerate, fluocinolone acetonide, halcinonide, betamethasone valerate, fluocinolone acetonide, hydrocortisone valerate, triamcinolone acetonide, hydrocortisone, oxicams, piroxicam, isoxicam, tenoxicam, sudoxicam, salicylates, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic, pyrazoles, phenylbutazone, oxyphenbutazone, feprazone, azapropazone and trimethazone, and any combinations thereof.

36. The foamable composition of claim 33 wherein the antiallergic agent is selected from the group comprising diphenhydramine, doxepin, phrilamine maleate, chlorpheniramine and tripelennamine, phenothiazines, promethazine hydrochloride, dimethindene maleate and any combination thereof at a therapeutically effective concentration.

37. The foamable composition of claim 14, wherein said active agent is an anticancer agent.

38. The foamable composition of claim 14, wherein the active agent is a photodynamic therapy agent.

39. The foamable composition of claim 14, wherein said active agent is a local anesthetic.

40. The foamable composition of claim 39, wherein said local anesthetic is selected from the group comprising benzocaine, lidocaine, bupivacaine, chlorprocaine, dibucaine, etidocaine, mepivacaine, tetracaine, dyclonine, hexylcaine, procaine, cocaine, ketamine, pramoxine, phenol 41. The foamable composition of claim 14, wherein the active agent is a retinoid.

42. The foamable composition of claim 41, wherein said retinoid is selected from the group comprising retinol, retinal, all trans retinoic acid, etretinate, actiretin, isotretinoin, adapalene and tazarotene.

43. The foamable composition of claim 14, wherein said active agent is an anti-wrinkle agent.

44. The foamable composition of claim 14, wherein said active agent is selected from the group comprising ascorbic acid and its salts, ascorbyl esters of fatty acids, magnesium ascorbyl phosphate, sodium ascorbyl phosphate, ascorbyl sorbate, tocopherol, tocopherol sorbate, tocopherol acetate, other esters of tocopherol, butylated hydroxy benzoic acids and their salts, 6-hydroxy-2,5,7,8-tetramethylchroman-2-carboxylic acid, gallic acid and its alkyl esters, propyl gallate, uric acid and its salts and alkyl esters, sorbic acid and its salts, lipoic acid, N,N-diethylhydroxylamine, amino-guanidine, sulfhydryl compounds, glutathione, dihydroxy fumaric acid and its salts, lycine pidolate, arginine pilolate, nordihydroguaiaretic acid, bioflavonoids, curcumin, lysine, methionine, proline, superoxide dismutase, silymarin, tea extract, grape skin/seed extract, melanin, and rosemary extract.

45. The foamable composition of claim 14, wherein said active agent is a self-tanning agent.

46. The foamable composition of claim 14, wherein said active agent is an anti-acne active agent.

47. The foamable composition of claim 46, wherein said active agent is selected from the group comprising resorcinol, sulfur, salicylic acid, salicylate salts, benzoyl peroxide, retinoic acid, isotretinoin, adapalene, tazarotene, azelaic acid and azelaic acid derivatives, antibiotic agents, erythromycin and clindamycin and zinc salts and complexes.

48. The foamable composition of claim 14, wherein said active agent is a skin whitening agents.

49. The foamable composition of claim 14, wherein said active agent is intended for transdermal delivery.

50. The foamable composition of claim 1 or 11, further comprising a foam adjuvant.

51. The foamable composition of claim 14, wherein, upon foaming of the foamable composition, an alcohol-free foam is obtained having a specific gravity of between about 0.01 g/mL and about 0.1 g/mL.

* * * * *

UNITED STATES PATENT AND TRADEMARK OFFICE
CERTIFICATE OF CORRECTION

Page 1 of 2

PATENT NO. : 7,700,076 B2
APPLICATION NO. : 10/922358
DATED : April 20, 2010
INVENTOR(S) : Tamarkin et al.

It is certified that error appears in the above-identified patent and that said Letters Patent is hereby corrected as shown below:

In the Specification

Column 3, Line 46, please delete "stain cloths" and insert --stain clothes--, therefor.

Column 12, Before Line 51, please insert header --Retinoid--, therefor.

Column 16, Line 49, please delete "[", therefor.

Column 18, Line 67, please delete "sheer force" and insert --shear force--, therefor.

Column 18, Line 67, please delete "Sheer-" and insert --Shear- --, therefor.

Column 21, Line 64, please insert --*-- before "In case of", therefor.

Column 22, between Lines 52 (after Density) and 53 (before Mineral oil), please insert the following header -- | Component | % w/w |
|---|---|
 --, therefor.

Column 23, between Lines 22 (after Density) and 23 (before Mineral oil), please insert the following header -- | Component | % w/w |
|---|---|
 --, therefor.

Column 23, between Lines 45 (after Density) and 46 (before Capric/caprylic triglycerides), please insert the following header -- | Component | % w/w |
|---|---|
 --, therefor.

Signed and Sealed this
Eleventh Day of February, 2014

Michelle K. Lee
*Deputy Director of the United States Patent and Trademark Office*

CERTIFICATE OF CORRECTION (continued)
U.S. Pat. No. 7,700,076 B2

Column 23, between Lines 54 (after Density) and 55 (before Capric/caprylic triglycerides), please insert the following header -- 
| Component | % w/w |
---, therefor.

Column 24, Line 2, please insert the following header

-- 
| Component | % w/w |
---, therefor.

Column 24, between Lines 15 (after Density) and 16 (before Capric/caprylic triglycerides), please insert the following header -- 
| Component | % w/w |
---, therefor.

Column 24, between Lines 48 (after Density) and 49 (before Isopropyl myristate), please insert the following header -- 
| Component | % w/w |
---, therefor.

Column 24, between Lines 59 (after Density) and 60 (before Capric/caprylic triglycerides), please insert the following header -- 
| Component | % w/w |
---, therefor.

Column 25, between Lines 7 (after Density) and 8 (before Capric/caprylic triglycerides), please insert the following header -- 
| Component | % w/w |
---, therefor.

Column 25, between Lines 38 (after Density) and 39 (before Capric/caprylic triglycerides), please insert the following header -- 
| Component | % w/w |
---, therefor.

Column 25, between Lines 47 (after Density) and 48 (before Capric/caprylic triglycerides), please insert the following header -- 
| Component | % w/w |
---, therefor.

Column 25, between Lines 58 (after Density) and 59 (before Capric/caprylic triglycerides), please insert the following header -- 
| Component | % w/w |
---, therefor.